United States Patent
Bosser Artal et al.

(10) Patent No.: US 12,297,186 B2
(45) Date of Patent: May 13, 2025

(54) BENZYLAMIDE DERIVATIVES AS INHIBITORS OF TRANSFORMING GROWTH FACTOR-BETA RECEPTOR I/ALK5

(71) Applicant: AGOMAB SPAIN, S.L.U., A Coruña (ES)

(72) Inventors: Ramón Bosser Artal, Barcelona (ES); Begoña Pampín Casal, A Coruña (ES); Julio Castro Palomino Laria, Barcelona (ES)

(73) Assignee: AGOMAB SPAIN, S.L.U., Toure a Coruña (ES)

( * ) Notice: Subject to any disclaimer, the term of this patent is extended or adjusted under 35 U.S.C. 154(b) by 497 days.

(21) Appl. No.: 17/780,099

(22) PCT Filed: Nov. 27, 2020

(86) PCT No.: PCT/EP2020/083566
§ 371 (c)(1),
(2) Date: May 26, 2022

(87) PCT Pub. No.: WO2021/105317
PCT Pub. Date: Jun. 3, 2021

(65) Prior Publication Data
US 2023/0025933 A1    Jan. 26, 2023

(30) Foreign Application Priority Data
Nov. 28, 2019   (EP) .................................... 19383057

(51) Int. Cl.
*C07D 401/14*     (2006.01)
*A61K 31/4709*    (2006.01)
*A61K 45/06*      (2006.01)

(52) U.S. Cl.
CPC ........ *C07D 401/14* (2013.01); *A61K 31/4709* (2013.01); *A61K 45/06* (2013.01)

(58) Field of Classification Search
CPC ... C07D 401/14; A61K 45/06; A61K 31/4709
See application file for complete search history.

(56) References Cited

FOREIGN PATENT DOCUMENTS

| | | | |
|---|---|---|---|
| CN | 110433164 A | 11/2019 | |
| EP | 0254866 A1 | 2/1988 | |
| WO | 02066462 A1 | 8/2002 | |
| WO | 2004026306 A2 | 4/2004 | |
| WO | WO-2004026302 A1 * | 4/2004 | ......... A61K 31/4439 |
| WO | 2004072033 A2 | 8/2004 | |
| WO | 2011076725 A1 | 6/2011 | |
| WO | 2012051361 A1 | 4/2012 | |
| WO | 2016172631 A2 | 10/2016 | |
| WO | 2019166616 A1 | 9/2019 | |
| WO | 2020033413 A2 | 2/2020 | |
| WO | 2022069509 A1 | 4/2022 | |

OTHER PUBLICATIONS

Jin, Cheng Hua, et al., Synthesis and biological evaluation of 1-substituted-3(5)-(6-methylpyridin-2-yl)-4-(quinolin-6-yl) byrazoles as transforming growth factor-β type 1 receptor kinase inhibitors. Bioorg Med Chem. Apr. 15, 2011;19 (8):2633-40. doi: 10.1016/j.bmc.2011.03.008. Epub Mar. 22, 2011. PMID: 21435890.
PCT International Search Report and Written Opinion; Application No. PCT/EP2020/083566 Origo Biopharma, S.L., International filing date of Nov. 27, 2020, date of mailing Jan. 19, 2021, 8 pages.
Akhurst, Rosemary J, and Akiko Hata. "Targeting the TGFbeta Signalling Pathway in Disease." Nature Reviews. Drug Discovery, vol. 11, No. 10, 2012, pp. 790-811.
Dewang, Purushottam M, and Dae-Kee Kim. "Synthesis and Biological Evaluation of 2-Pyridyl-Substituted Pyrazoles and Imidazoles as Transforming Growth Factor-β Type 1 Receptor Kinase Inhibitors." Bioorganic Medicinal Chemistry Letters, vol. 20, No. 14, 2010, pp. 4228-4232.

(Continued)

*Primary Examiner* — Jeffrey S Lundgren
*Assistant Examiner* — W. Justin Youngblood
(74) *Attorney, Agent, or Firm* — ArentFox Schiff LLP

(57) ABSTRACT

The present invention relates to novel benzylamide derivatives of formula (I)

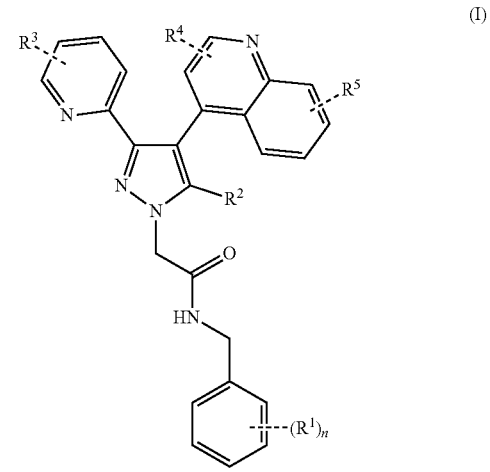

to processes for the preparation of said compounds; to pharmaceutical compositions comprising said compounds and to said compounds for use in the treatment of pathological conditions or diseases that can improve by inhibition of transforming growth factor-β receptor I (TGFβRI)/ALK5, such as diseases and disorders associated to fibrotic conditions of gastrointestinal system, skin and eyes, to methods for the treatment and/or prevention of said diseases or pathological conditions and to combinations comprising said compounds and further comprising therapeutically effective amounts of other therapeutic agents useful for the treatment of said diseases or pathological conditions.

34 Claims, No Drawings

(56) References Cited

OTHER PUBLICATIONS

Gellibert, Francoise, et al. "Identification of 1,5-Naphthyridine Derivatives as a Novel Series of Potent and Selective TGF-β Type I Receptor Inhibitors." Journal of Medicinal Chemistry, vol. 47, No. 18, 2004, pp. 4494-4506.

Jin, Cheng Hua, et al. "Discovery of N-((4-([1,2,4]Triazolo[1,5-a]Pyridin-6-Yl)-5-(6-Methylpyridin-2-Yl)-1H-Imidazol-2-Yl)Methyl)-2-Fluoroaniline (EW-7197): A Highly Potent, Selective, and Orally Bioavailable Inhibitor of TGF-β Type I Receptor Kinase as Cancer Immunotherapeutic/Antifibrotic Agent." Journal of Medicinal Chemistry, vol. 57, No. 10, 2014, pp. 4213-4238.

Li, Yan-Wei, et al. "Synthesis and Evaluation of the HIF-1α Inhibitory Activity of 3(5)-Substituted-4-(Quinolin-4-Yl)- and 4-(2-Phenylpyridin-4-Yl)Pyrazoles as Inhibitors of ALK5." Bioorganic Medicinal Chemistry Letters, vol. 30, No. 2, 2020, p. 126822.

Sawyer, J. Scott, et al. "Synthesis and Activity of New Aryl- and Heteroaryl-Substituted 5,6-Dihydro-4H-Pyrrolo[1,2-b] Pyrazole Inhibitors of the Transforming Growth Factor-β Type I Receptor Kinase Domain." Bioorganic Medicinal Chemistry Letters, vol. 14, No. 13, 2004, pp. 3581-3584.

Sawyer, J. Scott, et al. "Synthesis and Activity of New Aryl- and Heteroaryl-Substituted Pyrazole Inhibitors of the Transforming Growth Factor-β Type I Receptor Kinase Domain." Journal of Medicinal Chemistry, vol. 46, No. 19, 2003, pp. 3953-3956.

Zhu W.J. et al. "Design, synthesis, and antifibrosis evaluation of 4-(benzo-[c][1,2,5] thiadiazol-5-yl)-3(5)-(6-methyl-byridin-2-yl) pyrazole and 3(5)-(6-methylpyridin-2-yl)-4-(thieno-[3,2,-c]pyridin-2-yl)pyrazole derivatives." European Journal of Medicinal Chemistry, vol. 180, Jul. 5, 2019, p. 15.

Tojo M. et al., "The ALK-5 inhibitor A-83-01 inhibits SMAD signaling and epithelial-to-mesenchymal transition by transforming growth factor-B" Cancer Science, Oct. 17, 2005, vol. 96, No. 11, p. 791-800.

\* cited by examiner

BENZYLAMIDE DERIVATIVES AS INHIBITORS OF TRANSFORMING GROWTH FACTOR-BETA RECEPTOR I/ALK5

CROSS REFERENCE TO RELATED APPLICATIONS

This application is a national phase entry under 35 U.S.C. § 371 of International Patent Application PCT/EP2020/083566, filed Nov. 27, 2020, designating the United States of America and published in English as International Patent Publication WO 2021/105317 on Jun. 3, 2021, which claims the benefit under Article 8 of the Patent Cooperation Treaty to European Patent Application Serial No. 19383057.7, filed Nov. 28, 2019, the entireties of which are hereby incorporated by reference.

FIELD OF THE INVENTION

The present invention relates to novel benzylamide derivatives conveniently substituted, as potent inhibitors of transforming growth factor-β receptor I kinase, (also named activin receptor-like kinase 5) (TGFβRI)/ALK5.

The present invention also relates to a procedure for preparing these compounds; pharmaceutical compositions comprising an effective amount of these compounds; the use of the compounds for manufacturing a medicament for the treatment of pathological conditions or diseases that can improve by inhibition of transforming growth factor-βreceptor I (TGFβRI)/ALK5, such diseases or disorders are associated to fibrotic conditions of gastrointestinal system, skin and eyes.

STATE OF THE ART

Transforming growth factor-β (TGF-β) belongs to the TGF-β superfamily, which consists of TGF-β1, TGF-β2, TGF-β3, among other proteins. TGF-β is involved in many cellular processes, including cell proliferation, cell migration, invasion, epithelial-mesenchymal transition, extracellular matrix production and immune suppression. TGF-β and its receptors are often chronically overexpressed in various human diseases, including cancer, inflammation, tissue fibrosis and autoimmunity. Therefore, blockade of TGF-βsignalling pathway is considered an attractive target for drug development. (Heldin C. H. et al, *Signaling Receptors for TGF-b Family Members*, Cold Spring Harb Perspect Biol, 2016, doi: 10.1101/cshperspect.a022053). TGF-β signals via two related transmembrane type I and type II serine/threonine kinase receptors. Following TGF-β binding to the constitutively active type II receptor, the type I receptor (also called activin receptor-like kinase 5 (ALK5)) is phosphorylated and creates a binding site for Smad2 and Smad3 proteins, which are further phosphorylated. Phosphorylated Smad2/Smad3 proteins form a heteromeric complex with Smad4, which translocate into the nucleus, assembles with specific DNA-binding cofactors and co-modulators, and binds to the promoters of TGF-β target genes involved in cell differentiation, proliferation, apoptosis, migration, and extracellular matrix production. (Akhurst R. J. et al, *Targeting the TGFβ signalling pathway in disease*, Nature/Reviews, OCTOBER 2012, VOLUME 11).

In most cell types, activin receptor-like kinase 5-ALK5 (also known as TGFβR1) is the predominant TGF receptor I that is activated by TGF-β through TGFβ receptor II. This interaction requires both extracellular and intracellular domains for signal transduction. ALK5 and TGFβ receptor II proteins can also form active heterooligomeric complexes in the absence of ligand. These complexes are able to transduce basal signals when both receptors are co-expressed because of their intrinsic affinity for interaction. (Bierie B. et al, *TGF-β: the molecular Jekyll and Hyde of cancer*, Nature Reviews, Cancer, Volume 6, July 2006).

The functional TGFβRII-TGFβRI (ALK5) heteromeric signalling complex is commonly associated with human cancer, and it regulates the activation of downstream Smad-dependent and Smad-independent pathways. In fact, many studies have identified mutations in components that are associated with the TGF-β pathway, and which correlate with cancer occurrence and prognosis in many human tissues. The over expression of TGF-β1 has been associated with breast, colon, oesophageal, gastric, hepatocellular, lung and pancreatic cancer. Importantly, the overexpression of TGF-β in human cancer correlates with tumour progression, metastasis, angiogenesis and poor prognostic outcome.

Cancer

At present, the TGF-β pathway has been targeted using strategies that include the modification of immune components or the delivery of small-molecule inhibitors and soluble-protein or antisense-compound inhibitors. Immunotherapeutic strategies have been used to target the TGF-β pathway in animals.

The immunotherapy strategies used usually decrease TGF-β signalling in an immune component before reconstitution in a tumour-bearing recipient, thereby permitting a productive interaction with cancer cells. Alternatively, systemic delivery of compounds used to inhibit TGF-β usually abrogate all host-tumour interactions that are regulated by TGF-β including those involving immune evasion, angiogenesis, stromal-epithelial crosstalk and tumour-cell-autonomous signalling. Because of the immune-mediated disease and lethality associated with the genetic ablation or inhibition of TGF-β signalling in mice, it was unclear if inhibiting this pathway to treat cancer would be compatible with patient survival when delivered for a sustained duration in vivo. However, it has recently been shown that a lifetime exposure to systemic soluble TGF-β inhibitors in mouse models did not result in significant adverse effects. These studies have shown that TGF-βspecific inhibition should be compatible with long-term survival when given to humans for a sustained duration in vivo. (Yang, Y. et al, *Lifetime exposure to a soluble TGF-βantagonist protects mice against metastasis without adverse side effects*, J. Clin. Invest. 109:1607-1615 (2002)) and (Ruzek M. et al, *Minimal Effects on Immune Parameters Following Chronic Anti-TGF-b Monoclonal Antibody Administration to Normal Mice*, Immunopharmacology and Immunotoxicology Vol. 25, No. 2, pp. 235-257, 2003).

In the tumour microenvironment, TGF-β signalling affects several cell types such as immune cells, cancer-initiating cells, endothelial cells and fibroblasts. The overall effect of these microenvironment changes results in tumour progression and metastasis. TGF-β signalling is present in most malignancies, such as hepatocellular carcinoma, pancreatic cancer and myelodysplastic syndromes. Because of this prominent role, several small-molecule inhibitors have been developed to block the TGF-β signalling pathway with the intention to reduce tumour growth. (Rodon, J. et al, *First-in-Human Dose Study of the Novel Transforming Growth Factor-β Receptor I Kinase Inhibitor LY2157299 Monohydrate in Patients with Advanced Cancer and Glioma*, American Association for Cancer Research, Nov. 25, 2014; doi: 10.1158/1078-0432.CCR-14-1380).

Hepatocellular carcinoma (HCC) is a highly malignant cancer that is the third most frequent cause of tumour-related death in the United States and Europe. Current therapeutic options are invasive and aim to physically remove or destroy the tumour mass. However, later recurrence and/or metastatic spread are common and negatively affect survival. The overall prognosis is still unsatisfactory, and little progress has been made in finding new treatment options. In HCC patients, TGF-β has been reported to be over expressed in both blood and urine, correlating with a worse prognosis and survival and thus representing a marker of this cancer. It has been shown that TGF-β plays a key role in modulating HCC aggressiveness by triggering the epithelial to mesenchymal transition (EMT) of the cells. The studies have suggested that inhibition of the TGF-β pathway with small molecules inhibitors may be a promising therapy in HCC patients. (Fransvea, E. et al, *Blocking Transforming Growth Factor-β Up-Regulates E-Cadherin and Reduces Migration and Invasion of Hepatocellular Carcinoma Cells*, Wiley InterScience, 2008, doi 10.1002/hep.22201).

Pancreatic adenocarcinoma is one of leading cause of cancer mortality among adults in worldwide. For all stages combined, the 5-year survival rate is 5% and the median survival duration after diagnosis is <6 months. At the time of diagnosis, two thirds of patients present with locally advanced or metastatic disease. Even when pancreatic cancer is apparently localized to the pancreas and surgically removed, 70% of patients will develop liver metastases. Hence, pancreatic cancer poses one of the greatest challenges in cancer research. Particularly, human pancreatic cancer demonstrating increased levels of TGF-β has been found to be significantly associated with venous invasion, advanced tumour stages, progressive disease, shorter patient survival duration, and liver metastases. These creation of TGF-β by pancreatic tumours hampers an effective antitumor immune response by affecting the phenotype and function of dendritic cells in the tumour microenvironment. There are studies indicating that inhibition of TGF-β signalling cascades by the systemic administration of the novel small molecule-selective TGFRI/II kinase inhibitor LY2109761 suppresses liver and other abdominal site metastasis in an in vivo model of human pancreatic cancer. (Melisi, D. et al, *LY2109761, a novel transforming growth factor β receptor type I and type II dual inhibitor, as a therapeutic approach to suppressing pancreatic cancer metastasis*, Mol Cancer Ther 2008; 7(4). April 2008).

Colorectal cancer, also known as colon cancer, has particular features in the tumour microenvironment, such as lack of T-cell infiltration, low type 1 T-helper cell (TH1) activity and reduced immune cytotoxicity or increased TGF-β levels. Recent studies have shown that increased TGF-β in the tumour microenvironment represents a primary mechanism of immune evasion that promotes T-cell exclusion and blocks acquisition of the TH1-effector phenotype. Immunotherapies directed against TGF-β signalling may therefore have broad applications in treating patients with advanced colorectal cancer. (Tauriello D. V. F, et al, *TGF-β drives immune evasion in genetically reconstituted colon cancer metastasis*, Nature, Published online: 14 Feb. 2018, doi:10.1038/nature25492).

Meningiomas are approximately 36 percent of primary brain tumours. The absence of viable chemotherapies has prompted the search for novel therapies targeting growth regulatory cytokines. Of these, members of transforming growth factor beta (TGF-β) super-family may be particularly relevant. Higher grade, particularly anaplastic meningiomas have the highest recurrence rate and least response to any current therapy of any grade meningioma. Restoring TGF-β inhibitory signalling pathways may be an important component to the development of effective chemotherapies for meningiomas. To date, direct therapeutic options are limited, in part, due to toxicities associated with restoring TGF-β baseline inhibition. Nonetheless, in malignancies where TGF-β switches from inhibitory effects to promotion of tumor progression, TGF-β signalling may be blocked small molecule inhibitors of the TGF-β type I receptor. Preliminary studies suggest LY 2157229 (Galunisertib) is effective in blocking TGF-β effects. (Johnson, M. D. *Transforming growth factor β family in the pathogenesis of meningiomas*, World Neurosurgery, doi: 10.1016/j.wneu.2017.03.058).

Galunisertib is a TGFβRI kinase inhibitor currently under clinical development for a variety of cancers (Herbertz, S et al, *Clinical development of galunisertib (LY2157299 monohydrate), a small molecule inhibitor of transforming growth factor-beta signaling pathway*, Drug Design, Development and Therapy 2015:9 4479-4499). Inhibits TGFβRI/Alk5 kinase domain with $IC_{50}$ of 0.172 μM, ALK4 with $IC_{50}$ of 0.77 μM. Also inhibits a range of other kinases with submicromolar $IC_{50S}$ including MINK, TGFβRII, ALK6 and ACVR2B. There are earlier reports showing high doses of these compound were associated with adverse effects in rats and dogs. Thus, high stringency was recommended in the selection of dosing regimens in human subjects to achieve the desired effect with minimal toxicity. This compound is orally bioavailable. (Yingling, J. M. et al, *Preclinical assessment of galunisertib (LY2157299 monohydrate), a first-in-class transforming growth factor-β receptor type I inhibitor*, Oncotarget. 2018 Jan. 23; 9(6): 6659-6677).

Other inhibitor of TGF-β Type I Receptor Kinase under clinical development is EW-7197, which inhibits ALK5 with $IC_{50}$ value of 0.013 μM in a kinase assay. It is a highly selective ALK5/ALK4 inhibitor and in pharmacokinetic study in rats shows an oral bioavailability of 51% with high systemic exposure. (Jin, C. H. et al, *Discovery of N-((4-([1, 2,4]Triazolo[1,5-a]pyridin-6-y0-5-(6-methylpyridin-2-yl)-1H-imidazol-2-yl)methyl)-2-fluoroaniline (EW-7197): A Highly Potent, Selective, and Orally Bioavailable Inhibitor of TGF-β Type I Receptor Kinase as Cancer Immunotherapeutic/Antifibrotic Agent*, J. Med. Chem. 2014, 57, 4213-4238).

Fibrotic Conditions

Extensive evidence suggests that the canonical ALK5/Smad3 pathway is critically involved in the pathogenesis of fibrosis in many tissues. Oral administration of a small molecular weight selective inhibitor of the kinase activity of ALK5 inhibited fibrogenesis in a rat model of progressive TGF-β1-induced pulmonary fibrosis. Furthermore, Smad3 null mice exhibit attenuated fibrosis in a wide range of experimental models and are resistant to bleomycin-induced pulmonary fibrosis. Similarly, dermal fibrosis following irradiation, renal interstitial fibrosis produced by unilateral ureteral obstruction and cardiac fibrosis are all attenuated in Smad3-deficient animals. (Biernacka, A. et al, *TGF-βsignaling in fibrosis*, Growth Factors. 2011 October; 29(5): 196-202. doi:10.3109/08977194.2011.595714).

Inhibitors of TGF-β intracellular signalling pathway are useful treatments for fibroproliferative diseases. Specifically, fibroproliferative diseases include kidney disorders associated with unregulated TGF-β activity and excessive fibrosis including glomerulonephritis (GN), such as mesangial proliferative GN, immune GN and crescentic GN. Other renal conditions include diabetic nephropathy, renal interstitial fibrosis, renal fibrosis in transplant patients. Collagen vascular disorders include progressive systemic sclerosis, polymyositis and scleroderma. Autoimmune disorders associated with fibroproliferative characteristics are systemic lupus erythematosus and rheumatoid arthritis.

Myelofibrosis (MF) is a bone marrow disorder characterized by clonal myeloproliferation, aberrant cytokine production, extramedullary hematopoiesis, and bone marrow fibrosis. Although somatic mutations in Janus Kinase 2 (JAK2), Myeloproliferative Leukemia Virus (MPL), and Calreticulin gene (CALR) have been identified in the pathogenesis of these diseases, inhibitors of the JAK2 pathway have not demonstrated efficacy in ameliorating MF in patients. TGF-β family members are profibrotic cytokines and significant TGF-β1 isoform over expression was observed in a large cohort of primary MF patient samples. It has been demonstrated that TGF-β1 stimulates the deposition of excessive collagen by mesenchymal stromal cells (MSCs) by activating the TGF-β receptor I kinase (ALK5)/Smad3 pathway. The use of Galunisertib, a clinically active ALK5 inhibitor, significantly improved MF in mouse models. The data demonstrate the role of malignant hematopoietic stem cell (HSC)/TGF-β/MSC axis in the pathogenesis of MF and provide a preclinical rationale for ALK5 blockade as a therapeutic strategy in MF. (Yue, L. et al, *Efficacy of ALK5 inhibition in myelofibrosis*, JCI Insight. 2017; 2(6):e90932; doi.org/10.1172/jci.insight.90932).

Additionally, there are studies that have investigated the therapeutic potential of TGF-β inhibitors in preventing postsurgical peritoneal adhesion band formation, and the results show that these kind of compounds significantly attenuates adhesion band formation by inhibiting inflammation, oxidative stress, downregulation of proinflammatory genes as well as suppression of fibrosis and profibrotic molecules. (Soleimani, A. et al, *Novel oral transforming growth factor β signaling inhibitor potently inhibits post-surgical adhesion band formation*, J Cell Physiol. 2019; 1-9).

Several small molecules that inhibit ALK5 have been developed and demonstrate encouraging results in animal models of renal fibrosis. However, questions remain over the homeostatic role of ALK5 signaling, and therefore the safety implications of targeting this enzyme. A study showed that immunohistochemical analysis revealed that in the heart, ALK5 expression was unique to the valves. Two compounds (AZ12601011 and AZ12799734) were tested in rats. Microscopic evaluation revealed heart valve lesions in response to treatment with either compounds. Both compounds induced histopathologic heart valve lesions characterized by haemorrhage, inflammation, degeneration, and proliferation of valvular interstitial cells. The pathology was observed in all animals, at all doses tested, and occurred in all four heart valves. Analysis of ALK5 in rat hearts revealed expression in the valves, but not in the myocardium. Compared to control animals, protein levels of ALK5 were unchanged in the heart valves of treated animals. These findings suggest that TGF-β signaling via ALK5 plays a critical role in maintaining heart valve integrity. (Anderton M J et al, *Induction of Heart Valve Lesions by Small-Molecule ALK5 Inhibitors*, Toxicologic Pathology, 39: 916-924, 2011).

In addition, another ALK-5 inhibitor, Galunisertib, was tested in both rats and dogs. In both, the heart and great vessels were identified as the major target organs for toxicity. Cardiovascular findings in F344 rats treated with LY2157299 included degenerative and inflammatory valvular lesions (valvulopathy), myocardial degeneration and necrosis, aortitis with rupture, vasculitis/perivasculitis, and increased heart weights. (Stauber et al, *Nonclinical Safety Evaluation of a Transforming Growth Factor β Receptor I Kinase Inhibitor in Fischer 344 Rats and Beagle Dogs*, J Clin Pract. 2014, 4:3).

Irritable Bowel Disease (IBD)

In the gut, many immune and non-immune cells produce TGF-β1 and almost all the mucosal cells are targeted by this cytokine. TGF-β1 is secreted as part of a latent complex, which comprises latency-associated peptide (LAP) and latent TGF-β binding protein. Data emerging from recent studies indicate clearly that transforming growth factor β1 is one of the key molecules involved in the regulation of the epithelial cell biology and immunity in the gut.

These studies underline the crucial role of TGF-β1 in the maintenance of intestinal homeostasis and suggest that defective function of this cytokine can contribute to trigger and/or amplify detrimental signals in the gut (Troncone E. et al, *Transforming Growth Factor-β1/Smad7 in intestinal immunity, inflammation, and Cancer*, Front. Immunol. 9:1407, 2018).

Until now, researchers have studied the mechanisms of inflammation to alleviate and to inhibit intestinal fibrosis. However, anti-inflammatory agents have various problems and limitations to relieve or to treat fibrosis in inflammatory bowel disease (IBD). Therefore, in order to treat fibrotic diseases, new approaches for anti-fibrotic mechanisms should be explored. Numerous publications have displayed that molecules related to TGF-β signalling were implicated in fibrosis, so it is an important target in the progression of intestinal fibrosis because it correlates with the complex and diverse signalling pathways regulating the mechanism of the progression of intestinal fibrosis in IBD. Therefore, TGF-β signalling is a potential strategy to treat and alleviate fibrosis in several fibrotic diseases including IBD. (Yun S. M. et al, *The Molecular Mechanism of Transforming Growth Factor-β Signaling for Intestinal Fibrosis: A Mini-Review*, Frontiers in Pharmacology, Mini-Review, published: 27 Feb. 2019; Binabaj M. M et al, *EW-7197 prevents ulcerative colitis-associated fibrosis and inflammation*, J Cell Physiol. 2018; 1-8).

Eye Diseases

Transforming growth factor-β (TGF-β) may play a role in the pathogenesis of primary open-angle glaucoma (POAG). TGF-β has been implicated in the pathogenesis of POAG, and potential areas for TGF-β targeting include production, activation, downstream signalling and local regulation. Elevated levels of TGF-β are found in the aqueous humor and in reactive optic nerve astrocytes in patients with glaucoma. Although recent research has revealed many unknowns, a deeper understanding of TGF-β's cellular signalling pathways is necessary for designing potential TGF-β intervention strategies. (Wang, J. et al, *Targeting Transforming Growth Factor-b Signaling in Primary Open-Angle Glaucoma*, J Glaucoma 2017; 26:390-395).

Eye diseases associated with a fibroproliferative condition include retinal reattachment surgery accompanying proliferative vitreoretinopathy, cataract extraction with intraocular lens implantation, and post-glaucoma drainage surgery are associated with TGF-β1 overproduction.

The authors of the present invention have developed new benzylamide derivatives conveniently substituted as potent inhibitors of TGF-β signalling pathway, particularly as inhibitors of transforming growth factor-β receptor I/activin-like kinase 5 (TGFβRI/ALK5), having low systemic exposure which facilitates the avoidance of significant well-known side effects. Therefore, the present invention discloses ALK5 inhibitors with low systemic exposure conferring them a good therapeutic window.

SUMMARY OF THE INVENTION

In one of its aspects (aspect 1), the present invention refers to novel benzylamide derivatives conveniently substituted of formula (I):

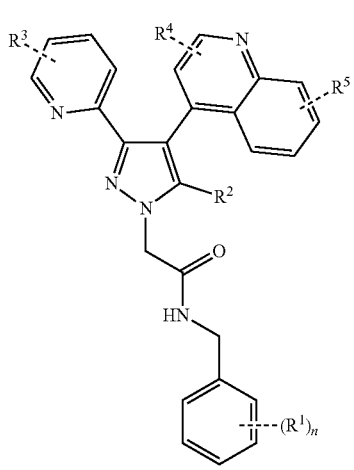

(I)

wherein:
$R^1$ represents independently 1 or 2 groups selected from:
a) halogen atom,
b) linear or branched $C_1$-$C_6$ alkyl optionally substituted by 1, 2 or 3 halogen atoms,
c) cyano group,
d) $C_1$-$C_3$ alkoxy,
e) —COOH,
$R^2$ represent a group selected from:
a) hydrogen atom,
b) $C_1$-$C_3$ alkyl,
c) $C_3$-$C_4$ cycloalkyl,
$R^3$ represents a group selected from:
a) $C_1$-$C_3$ alkyl optionally substituted by 1, 2 or 3 halogen atoms,
b) hydrogen atom,
c) halogen atom,
$R^4$ and $R^5$ independently represent a group selected from:
a) hydrogen atom,
b) $C_1$-$C_3$ alkyl optionally substituted by 1, 2 or 3 halogen atoms,
c) halogen atoms,
n has a value of 0, 1 or 2 and pharmaceutically acceptable salts thereof.

In a second aspect the present invention relates to processes for the preparation of the compounds of aspect 1.

In a third aspect the present invention relates to pharmaceutical compositions comprising a compound of aspect 1 and a pharmaceutical aspect diluent or carrier.

In a fourth aspect the present invention relates to pharmaceutical compositions according to the third aspect described above which further comprise a therapeutically effective amount of a therapeutic agent selected from agent useful for the treatment of gastrointestinal diseases, such as inflammatory bowel diseases among there are Crohn's disease and ulcerative colitis, hepatic fibrosis and cancer, specifically gastric cancer, esophageal cancer and colorectal cancer; fibrotic skin diseases, such as scleroderma, nephrogenic fibrosing dermopathy, mixed connective tissue disease, scleromyxedema, scleredema, and eosinophilic fasciitis; fibrotic eye diseases such as dry eyes, age-related macular degeneration, scarring in the cornea and conjunctiva, post-cataract fibrosis, proliferative vitreoretinopathy and proliferative diabetic retinopathy.

In a fifth aspect the present invention relates to the use of the compound of aspect 1 in the manufacture of a medicament for the treatment and/or prevention of a disease or pathological condition that can be ameliorated by inhibition of transforming growth factor-β receptor I (TGFβRO/ALK5, such as gastrointestinal diseases, such as inflammatory bowel diseases among there are Crohn's disease and ulcerative colitis, hepatic fibrosis and cancer, specifically gastric cancer, esophageal cancer and colorectal cancer; fibrotic skin diseases, such as scleroderma, nephrogenic fibrosing dermopathy, mixed connective tissue disease, scleromyxedema, scleredema, and eosinophilic fasciitis; fibrotic eye diseases such as dry eyes, age-related macular degeneration, scarring in the cornea and conjunctiva, post-cataract fibrosis, proliferative vitreoretinopathy and proliferative diabetic retinopathy.

In a sixth aspect the present invention relates to methods for the treatment and/or prevention of diseases or pathological conditions that can be ameliorated by inhibition of transforming growth factor-β receptor I (TGFβRO/ALK5, such as gastrointestinal diseases, such as inflammatory bowel diseases among there are Crohn's disease and ulcerative colitis, hepatic fibrosis and cancer, specifically gastric cancer, esophageal cancer and colorectal cancer; fibrotic skin diseases, such as scleroderma, nephrogenic fibrosing dermopathy, mixed connective tissue disease, scleromyxedema, scleredema, and eosinophilic fasciitis; fibrotic eye diseases such as dry eyes, age-related macular degeneration, scarring in the cornea and conjunctiva, post-cataract fibrosis, proliferative vitreoretinopathy and proliferative diabetic retinopathy.

In a seventh aspect the present invention relates to a combination product of the compound of the first aspect described above with one more therapeutic agent known to be useful in the treatment of diseases selected from such as gastrointestinal diseases, such as inflammatory bowel diseases among there are Crohn's disease and ulcerative colitis, hepatic fibrosis and cancer, specifically gastric cancer, esophageal cancer and colorectal cancer; fibrotic skin diseases, such as scleroderma, nephrogenic fibrosing dermopathy, mixed connective tissue disease, scleromyxedema, scleredema, and eosinophilic fasciitis; fibrotic eye diseases such as dry eyes, age-related macular degeneration, scarring in the cornea and conjunctiva, post-cataract fibrosis, proliferative vitreoretinopathy and proliferative diabetic retinopathy.

In an eighth aspect the present invention relates to the compound of aspect 1 for use in the treatment and/or prevention of a disease or pathological condition that can be ameliorated by inhibition of transforming growth factor-β receptor I (TGFβRO/ALK5, such as gastrointestinal diseases, such as inflammatory bowel diseases among there are Crohn's disease and ulcerative colitis, hepatic fibrosis and cancer, specifically gastric cancer, esophageal cancer and colorectal cancer; fibrotic skin diseases, such as scleroderma, nephrogenic fibrosing dermopathy, mixed connective tissue disease, scleromyxedema, scleredema, and eosinophilic fasciitis; fibrotic eye diseases such as dry eyes, age-related macular degeneration, scarring in the cornea and conjunctiva, post-cataract fibrosis, proliferative vitreoretinopathy and proliferative diabetic retinopathy.

In a particular embodiment, the compounds of formula (I) have a low systemic exposure after oral, topical or ocular administration, due to its very low metabolic stability, leading to the formation of inactive metabolites. For this reason, they are especially suited for the treatment of diseases such as gastrointestinal diseases, including inflammatory bowel diseases among there are Crohn's disease and ulcerative colitis, hepatic fibrosis and cancer, specifically gastric cancer, esophageal cancer and colorectal cancer; fibrotic skin diseases, such as scleroderma, nephrogenic fibrosing dermopathy, mixed connective tissue disease, scleromyxedema, scleredema, and eosinophilic fasciitis; fibrotic eye diseases such as dry eyes, age-related macular degeneration, scarring in the cornea and conjunctiva, post-cataract fibrosis, proliferative vitreoretinopathy and proliferative diabetic retinopathy.

As it is said before, the benzylamide derivatives of the present invention are useful in the treatment or prevention of diseases known to be susceptible to amelioration by treatment with inhibitor of transforming growth factor-β receptor I (TGFβRI)/ALK5, such as gastrointestinal diseases, such as inflammatory bowel diseases among there are Crohn's disease and ulcerative colitis, hepatic fibrosis and cancer, specifically gastric cancer, esophageal cancer and colorectal cancer; fibrotic skin diseases, such as scleroderma, nephrogenic fibrosing dermopathy, mixed connective tissue disease, scleromyxedema, scleredema, and eosinophilic fasciitis; fibrotic eye diseases such as dry eyes, age-related macular degeneration, scarring in the cornea and conjunctiva, post-cataract fibrosis, proliferative vitreoretinopathy and proliferative diabetic retinopathy.

Accordingly, the derivatives of the present invention and pharmaceutically acceptable salts thereof, and pharmaceutical compositions comprising such compounds and/or salts thereof, may be used in a method of treatment of pathological conditions or disease of human body which comprises administering to a subject in need of said treatment, an effective amount of the benzylamide derivatives of the invention or a pharmaceutically acceptable salt thereof.

As used herein, the term $C_a$-$C_b$ alkyl includes linear or branched radicals, having from a to b carbon atoms. Preferred radicals have from 1 to 6 carbon atoms, preferably from 1 to 4 carbon atoms. Examples of linear or branched alkyl groups are methyl, ethyl, n-propyl, iso-propyl, n-butyl, i-butyl, sec-butyl, tert-butyl, pentyl and hexyl.

As used herein, the term linear or branched $C_a$-$C_b$ alkoxy is used to designate radicals which contain $C_a$-$C_b$ alkyl radicals linked to an oxygen atom ($C_xH_{2x+1}$—O—. Preferred radicals have from 1 to 6 carbon atoms, preferably from 1 to 4 carbon atoms. Preferred alkoxy radicals include for example, methoxy, ethoxy, n-propoxy, i-propoxy.

As used herein, the term halogen atom includes chlorine, fluorine, bromine and iodine atoms, preferably fluorine, chlorine and bromine atoms. The term halo, when used as a prefix, has the same meaning. As a mere example haloalkyl means an alkyl substituted by one or more halogen atoms.

As used herein, some of the atoms, radicals, chains or cycles present in the general structures of the invention are "optionally substituted". This means that these atoms, radicals, chains or cycles can be either unsubstituted or substituted in any position by one or more, for example 1, 2, 3 or 4, substituents, whereby the hydrogen atoms bound to the unsubstituted atoms, radicals, chains or cycles are replaced by chemically acceptable atoms, radicals, chains or cycles. When two or more substituents are present, each substituent may be the same or different.

As used herein, the term pharmaceutically acceptable salt is used to designate salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluensulphonic acid. Pharmaceutically acceptable bases include alkali metal (e.g. sodium or potassium), alkali earth metal (e.g. calcium or magnesium) hydroxides, and organic bases, for example alkyl amines, arylalkyl amines and heterocyclic amines.

Other preferred salts according to the invention are quaternary ammonium compounds wherein an equivalent of an anion ($X^{-n}$) is associated with the positive charge of the N atom. $X^{-n}$ may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulfonate and p-toluenesulphonate. $X^{-n}$ is preferably an anion selected from chloride, bromide, iodide, sulphate, nitrate, acetate, maleate, oxalate, succinate or trifluoroacetate. More preferably, $X^-$ is chloride, bromide, trifluoroacetate or methanesulfonate.

According to one embodiment of the present invention in the compounds of formula (I), each $R^1$ independently represents a halogen atom. In a preferred embodiment n is 0 or n is 1 or 2 and each $R^1$ represents a halogen atom. In a more preferred embodiment, n is 1 or 2 and each $R^1$ represents a fluorine or chlorine atom.

According to one embodiment of the present invention in the compounds of formula (I), $R^2$ represents a hydrogen atom.

According to one embodiment of the present invention in the compounds of formula (I), $R^3$ represents a group selected from $C_1$-$C_3$ alkyl optionally substituted by 1, 2 or 3 halogen atoms, and hydrogen atom. In a preferred embodiment, $R^3$ represents hydrogen or a $C_1$-$C_3$ alkyl. In a more preferred embodiment, $R^3$ represents hydrogen, a methyl group or an ethyl group, preferably hydrogen or a methyl group.

According to one embodiment of the present invention in the compounds of formula (I), $R^4$ represents a hydrogen atom.

According to one embodiment of the present invention in the compounds of formula (I), $R^2$, $R^4$ and $R^5$ represent hydrogen atoms.

According to one embodiment of the present invention in the compounds of formula (I), n is 0 or n is 1 or 2 and each $R^1$ independently represents a halogen atom, $R^2$, $R^4$ and $R^5$ independently represent hydrogen atoms, and $R^3$ represents a group selected from methyl group, ethyl group and hydrogen atom. In a preferred embodiment n is 0 or n is 1 or 2 and each $R^1$ represents a halogen atom and $R^3$ represents a methyl group. In a more preferred embodiment, n is 1 or 2 and each $R^1$ independently represents a fluorine or a chlorine atom.

Particular individual compounds of the present invention include:
N-benzyl-2-(3-(pyridin-2-yl)-4-(quinolin-4-yl)-1H-pyrazol-1-yl)acetamide
N-(4-fluorobenzyl)-2-(3-(pyridin-2-yl)-4-(quinolin-4-yl)-1H-pyrazol-1-yl)acetamide
N-(4-chlorobenzyl)-2-(3-(pyridin-2-yl)-4-(quinolin-4-yl)-1H-pyrazol-1-yl)acetamide
N-(4-bromobenzyl)-2-(3-(pyridin-2-yl)-4-(quinolin-4-yl)-1H-pyrazol-1-yl)acetamide
N-(4-cyanobenzyl)-2-(3-(pyridin-2-yl)-4-(quinolin-4-yl)-1H-pyrazol-1-yl)acetamide
N-(4-methoxybenzyl)-2-(3-(pyridin-2-yl)-4-(quinolin-4-yl)-1H-pyrazol-1-yl)acetamide
N-(4-methylbenzyl)-2-(3-(pyridin-2-yl)-4-(quinolin-4-yl)-1H-pyrazol-1-yl)acetamide
N-(4-(tert-butyl)benzyl)-2-(3-(pyridin-2-yl)-4-(quinolin-4-yl)-1H-pyrazol-1-yl)acetamide
N-benzyl-2-(3-(6-methylpyridin-2-yl)-4-(quinolin-4-yl)-1H-pyrazol-1-yl)acetamide
N-(3-methylbenzyl)-2-(3-(pyridin-2-yl)-4-(quinolin-4-yl)-1H-pyrazol-1-yl)acetamide
N-(3-fluorobenzyl)-2-(3-(pyridin-2-yl)-4-(quinolin-4-yl)-1H-pyrazol-1-yl)acetamide
N-(3-chlorobenzyl)-2-(3-(pyridin-2-yl)-4-(quinolin-4-yl)-1H-pyrazol-1-yl)acetamide N-(3-cyanobenzyl)-2-(3-(pyridin-2-yl)-4-(quinolin-4-yl)-1H-pyrazol-1-yl)acetamide N-(2-methylbenzyl)-2-(3-(pyridin-2-yl)-4-(quinolin-4-yl)-1H-pyrazol-1-yl)acetamide N-(2-methylbenzyl)-2-(3-(6-methylpyridin-2-yl)-4-(quinolin-4-yl)-1H-pyrazol-1-yl)acetamide N-(2-fluorobenzyl)-2-(3-(pyridin-2-yl)-4-(quinolin-4-yl)-1H-pyrazol-1-yl)acetamide N-(2-fluorobenzyl)-2-(3-(6-methylpyridin-2-yl)-4-(quinolin-4-yl)-1H-pyrazol-1-yl)acetamide N-benzyl-2-(3-(6-ethylpyridin-2-yl)-4-(quinolin-4-yl)-1H-pyrazol-1-yl)acetamide 2-(3-(6-ethylpyridin-2-yl)-4-(quinolin-4-yl)-1H-pyrazol-1-yl)-N-(2-methylbenzyl)acetamide N-(4-methylbenzyl)-2-(3-(6-methylpyridin-2-yl)-4-(quinolin-4-yl)-1H-pyrazol-1-yl)acetamide N-(2-chlorobenzyl)-2-(3-(pyridin-2-yl)-4-(quinolin-4-yl)-1H-pyrazol-1-yl)acetamide N-(2-chlorobenzyl)-2-(3-(6-methylpyridin-2-yl)-4-(quinolin-4-yl)-1H-pyrazol-1-yl)acetamide N-(2,6-difluorobenzyl)-2-(3-(pyridin-2-yl)-4-(quinolin-4-yl)-1H-pyrazol-1-yl)acetamide N-(2,6-difluorobenzyl)-2-(3-(6-methylpyridin-2-yl)-4-(quinolin-4-yl)-1H-pyrazol-1-yl)acetamide N-(2,6-dimethylbenzyl)-2-(3-(pyridin-2-yl)-4-(quinolin-4-yl)-1H-pyrazol-1-yl)acetamide N-(2,6-dimethylbenzyl)-2-(3-(6-methylpyridin-2-yl)-4-(quinolin-4-yl)-1H-pyrazol-1-yl)acetamide N-(2-ethylbenzyl)-2-(3-(6-methylpyridin-2-yl)-4-(quinolin-4-yl)-1H-pyrazol-1-yl)acetamide N-(2,6-dichlorobenzyl)-2-(3-(6-methylpyridin-2-yl)-4-(quinolin-4-yl)-1H-pyrazol-1-yl)acetamide 4-((2-(3-(pyridin-2-yl)-4-(quinolin-4-yl)-1H-pyrazol-1-yl)acetamido)methyl)benzoic acid hydrochloride The compounds of the present invention can be prepared by using the procedures described below. To facilitate the description of the procedures, concrete examples have been used but they do not restrict in any way the scope of the present invention.

The synthesis of compound of formula (I) is outlined in Scheme 1.

Scheme 1

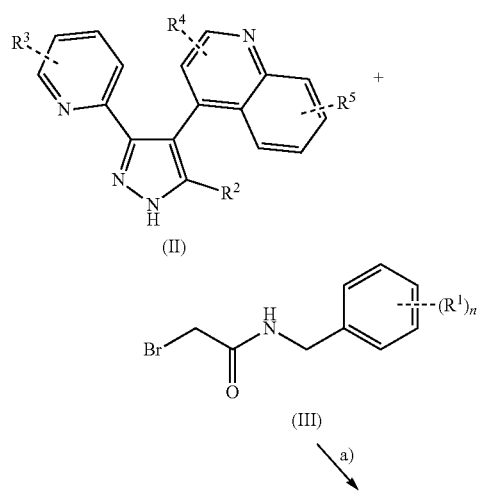

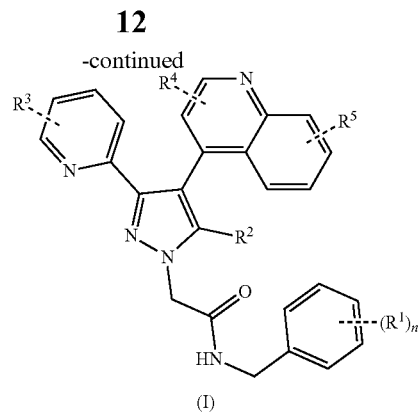

Reagents and conditions:
Stage a) NaH, THF, DMF, 0° C. to RT or $Na_2CO_3$, DMF, RT.

Compounds of general formula (I) are prepared in several stages from 4-(3-(pyridin-2-yl)-1H-pyrazol-4-yl)quinoline derivatives (II) by reaction with the corresponding bromoacetamide (III) (WO 2009123316 A1; Chem. Eur. J., 2013, 19(32), 10506-10510). Some 4-(3-(pyridin-2-yl)-1H-pyrazol-4-yl)quinoline derivatives (II) are commercially available and other can be prepared in several steps as is indicated in Scheme 2 (J. Med. Chem. 2004, 47, 4494-4506; WO 2004026302 A1).

Scheme 2

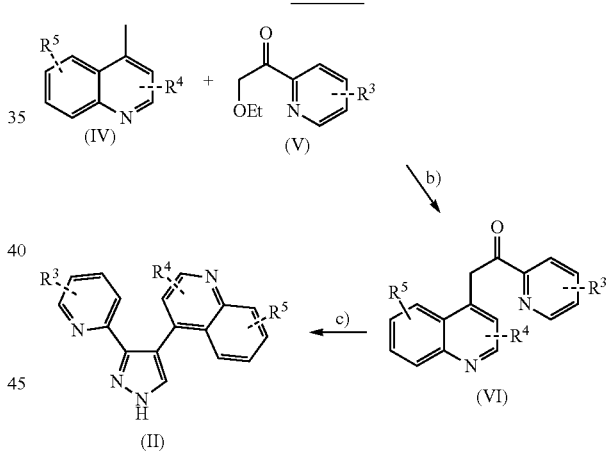

Reagents and conditions:
Stage b) LiHMDS, THF, −60° C. to −10° C.

Stage c) Compounds in which $R^4$=H. Step 1. DMF·DMA, AcOH, DMF, RT; Step 2. $N_2H_4 \cdot H_2O$, RT.

Compounds in which $R^2$=$C_3$-$C_4$ cycloalkyl optionally substituted by 1, 2 or 3 group selected from halogen atoms: Stage d) $R^2$—CO—$N_2H_3$, HCl, THF, 40° C., according to the following scheme (Scheme 2-1).

The 4-methylquinoline derivatives (IV) are condensed with ethyl 2-pyridinecarboxylate (V) in the presence of lithium bis(trimethylsilyl)amides to provide compounds of formula (VI). The reaction of the derivatives (VI) with dimethylformamide dimethylacetal affords to non-isolated enamine intermediates, which are cyclised directly by reaction with hydrazine in presence of acetic acid to provide pyrazoles of formula (II).

Another route to afford compounds of formula (II) is the following:

Scheme 2-1

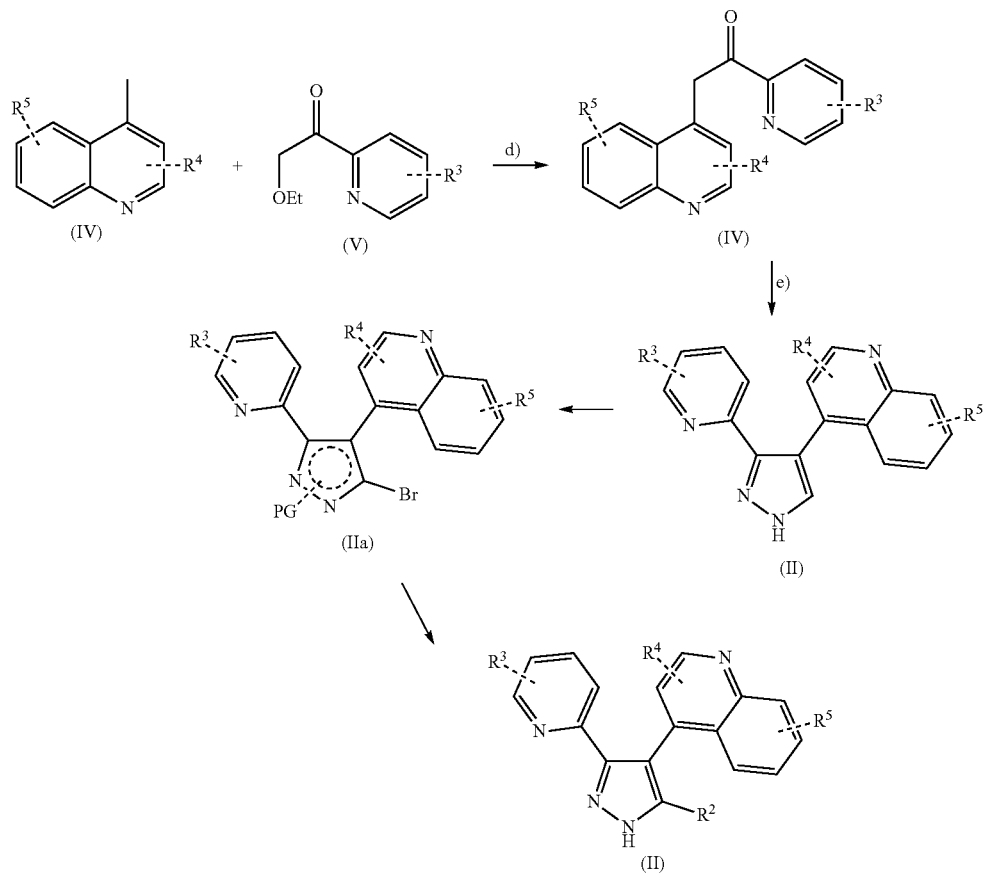

The pyrazole derivatives of formula (IIa) can be halogenated to give the corresponding halogenated compounds. These compounds afford compounds of formula (IIa) with standard halogenation reagents, as succinimide derivatives, after the protection of the nitrogen of the pyrazole ring. A C—C coupling followed of the deprotection of nitrogen of the pyrazole to give derivatives of formula (II). PG=protecting group. Protecting group are selected from Tetrahydropyran (THP), tert-butiloxicarbonilo (Boc) and Trytil group (Tr).

The bromoacetamides the formula (III) are readily synthesized in one stage from commercially available amines (VII) by reaction with bromoacetyl bromide the formula (VIII) as is indicated in Scheme 3(*J. Med. Chem.* 2009, 52, 6851-6859).

Scheme 3

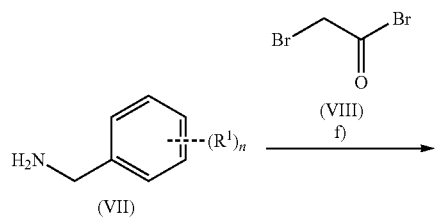

-continued

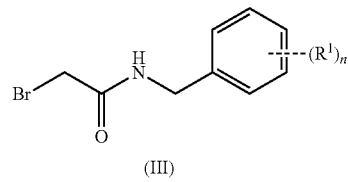

Reagents and conditions:

Stage f) THF, 0° C. to RT; or CH$_2$Cl$_2$, DIPEA, 0° C. to RT.

Other amines the formula (VII) are not commercially available can be prepared in several steps as is indicated in Scheme 4.

Compounds of formula (VII) are synthesized from compound of formula (IX) wherein X is a halogen atom, according to is described below in the Scheme 4.

Scheme 4

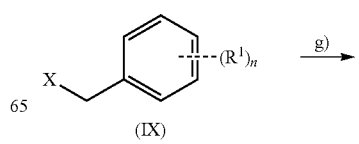

-continued

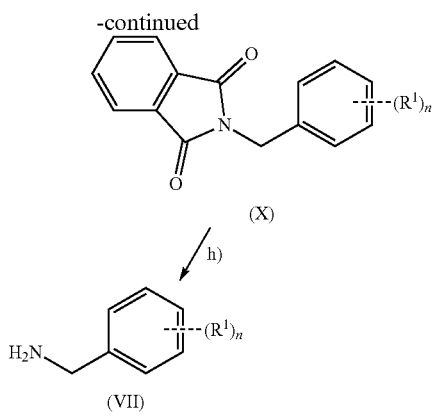

Reagents and conditions:
X: halogen atoms
Stage g) phthalimide, K₂CO₃, DMF 50° C.,
Stage h) N₂H₄·H₂O, EtOH, reflux.

The amines of formula (VII) are prepared using classical conditions of Gabriel synthesis; which involves the reaction of the conjugate base of phthalimide and an alkyl halide (IX) followed subsequent removal of the phthaloyl group with hydrazine to provide primary amines (VII).

Abbreviations

In the present application are used the following abbreviations, with the corresponding definitions:
AcOH: Acetic Acid
ACVR2B: activin A receptor, type IIB
ALKn: activin receptor-like kinase n
ATP: adenosin triphosphate
Boc₂O: t-butyl dicarbonate
Clint: Intrinsic clearance
DIPEA: N,N-Diisopropylethylamine
DMA: Dimethylacetamide
DMAP: 4-Dimethylaminopyridine
DME: Dimethoxyethane
DMF: Dimethylformamide
DMSO: Dimethyl sulfoxide
Et₃N: Triethylamine
EtOAc: Ethyl acetate
EtOH: ethanol
FBS: Fetal bovine serum
¹H-NMR: Proton nuclear magnetic resonance
K₂EDTA: ethylenediaminetetracetic acid dipotassium salt
KOtBu: Potassium tert-butoxide
LC: Liquid chromatography
LiHMDS: Lithium bis(trimethylsilyl)amide
LLOQ: lower limit of quantification
MeCN: Acetonitrile
MeOH: Methanol
MS: Mass spectroscopy
N₂H₄·H₂O: Hydrazine monohydrate
NaCMC: Sodium carboxymethyl cellulose
NMP: N-Methyl-2-pyrrolidone
PCy₃: tricyclohexylphosphine
Pd(OAc)₂: Palladium(II) acetate
Pd/C: Palladium on carbon
PPh₃: Triphenylphosphine
Rt: retention time
RT: room temperature
TGFβ: transforming growth factor-β
THF: Tetrahydrofuran THF:EtOH: Tetrahydrofuran:ethanol
UPLC: ultra high performance liquid chromatography
UV: Ultraviolet Pharmacological Activity In Vitro Enzyme Assay: Inhibition of TGFβR-1Kinase Activity Human TGFβ1 R-1 inhibition experiments were carried out in a white 384-microplate low flange (Corning 3572) with ADP-Glo kinase Assay Kit (Promega V9101) and TGβR-1 Kinase Enzyme System (Promega V4092). Test compounds and standard Galunisertib (Cayman 15312), 50 ng/well TGFβR-1 kinase and 50 μM ATP were added in a final volumen of 10 μL/well, using Reaction buffer supplied by kit as assay buffer. The reaction mixture was incubated in gentle shaking for 120 min at RT, after incubation of 10 μL of ADP-Glo Reagent was added and incubated in gentle shaking for 40 min at RT. 20 μL of Kinase Detection Reagent was added and plate was incubated in gentle shaking for 30 min at RT. Luminiscence (1000 ms) was measured in Perkin Elmer EnSpire Multimode plate reader.

Results

Table 1 shows the results of assays described below of some compounds of the present invention.

TABLE 1

| Example | Name | IC₅₀ range |
|---|---|---|
| 1 | N-benzyl-2-(3-(pyridin-2-yl)-4-(quinolin-4-yl)-1H-pyrazol-1-yl)acetamide | A |
| 2 | N-(4-fluorobenzyl)-2-(3-(pyridin-2-yl)-4-(quinolin-4-yl)-1H-pyrazol-1-yl)acetamide | B |
| 3 | N-(4-chlorobenzyl)-2-(3-(pyridin-2-yl)-4-(quinolin-4-yl)-1H-pyrazol-1-yl)acetamide | B |
| 4 | N-(4-bromobenzyl)-2-(3-(pyridin-2-yl)-4-(quinolin-4-yl)-1H-pyrazol-1-yl)acetamide | B |
| 7 | N-(4-methylbenzyl)-2-(3-(pyridin-2-yl)-4-(quinolin-4-yl)-1H-pyrazol-1-yl)acetamide | B |
| 9 | N-benzyl-2-(3-(6-methylpyridin-2-yl)-4-(quinolin-4-yl)-1H-pyrazol-1-yl)acetamide | A |
| 10 | N-(3-methylbenzyl)-2-(3-(pyridin-2-yl)-4-(quinolin-4-yl)-1H-pyrazol-1-yl)acetamide | B |
| 11 | N-(3-fluorobenzyl)-2-(3-(pyridin-2-yl)-4-(quinolin-4-yl)-1H-pyrazol-1-yl)acetamide | B |
| 12 | N-(3-chlorobenzyl)-2-(3-(pyridin-2-yl)-4-(quinolin-4-yl)-1H-pyrazol-1-yl)acetamide | B |
| 13 | N-(3-cyanobenzyl)-2-(3-(pyridin-2-yl)-4-(quinolin-4-yl)-1H-pyrazol-1-yl)acetamide | B |
| 14 | N-(2-methylbenzyl)-2-(3-(pyridin-2-yl)-4-(quinolin-4-yl)-1H-pyrazol-1-yl)acetamide | B |
| 15 | N-(2-methylbenzyl)-2-(3-(6-methylpyridin-2-yl)-4-(quinolin-4-yl)-1H-pyrazol-1-yl)acetamide | A |
| 16 | N-(2-fluorobenzyl)-2-(3-(pyridin-2-yl)-4-(quinolin-4-yl)-1H-pyrazol-1-yl)acetamide | B |
| 17 | N-(2-fluorobenzyl)-2-(3-(6-methylpyridin-2-yl)-4-(quinolin-4-yl)-1H-pyrazol-1-yl)acetamide | B |
| 18 | N-benzyl-2-(3-(6-ethylpyridin-2-yl)-4-(quinolin-4-yl)-1H-pyrazol-1-yl)acetamide | A |
| 19 | 2-(3-(6-ethylpyridin-2-yl)-4-(quinolin-4-yl)-1H-pyrazol-1-yl)-N-(2-methylbenzyl)acetamide | A |
| 20 | N-(4-methylbenzyl)-2-(3-(6-methylpyridin-2-yl)-4-(quinolin-4-yl)-1H-pyrazol-1-yl)acetamide | A |
| 21 | N-(2-chlorobenzyl)-2-(3-(pyridin-2-yl)-4-(quinolin-4-yl)-1H-pyrazol-1-yl)acetamide | B |
| 22 | N-(2-chlorobenzyl)-2-(3-(6-methylpyridin-2-yl)-4-(quinolin-4-yl)-1H-pyrazol-1-yl)acetamide | A |
| 23 | N-(2,6-difluorobenzyl)-2-(3-(pyridin-2-yl)-4-(quinolin-4-yl)-1H-pyrazol-1-yl)acetamide | B |
| 24 | N-(2,6-difluorobenzyl)-2-(3-(6-methylpyridin-2-yl)-4-(quinolin-4-yl)-1H-pyrazol-1-yl)acetamide | A |

TABLE 1-continued

| Example | Name | IC$_{50}$ range |
|---|---|---|
| 25 | N-(2,6-dimethylbenzyl)-2-(3-(pyridin-2-yl)-4-(quinolin-4-yl)-1H-pyrazol-1-yl)acetamide | A |
| 26 | N-(2,6-dimethylbenzyl)-2-(3-(6-methylpyridin-2-yl)-4-(quinolin-4-yl)-1H-pyrazol-1-yl)acetamide | A |
| 27 | N-(2-ethylbenzyl)-2-(3-(6-methylpyridin-2-yl)-4-(quinolin-4-yl)-1H-pyrazol-1-yl)acetamide | A |
| 28 | N-(2,6-dichlorobenzyl)-2-(3-(6-methylpyridin-2-yl)-4-(quinolin-4-yl)-1H-pyrazol-1-yl)acetamide | A |
| 29 | 4-((2-(3-(pyridin-2-yl)-4-(quinolin-4-yl)-1H-pyrazol-1-yl)acetamido)methyl)benzoic acid hydrochloride | B |

Ranges:
A: IC$_{50}$ =<100 nM
B: 100 nM < IC$_{50}$ < 800 nM

Determination of the Intracellular TGF-beta Kinase Activity (ALK-5)

The experiments were carried out in A549 cell line. 30000 cells were seeded in 200 µl of culture medium (Sigma D6046) supplemented with L-Glutamine (Sigma G7513), Penicillin/Streptomycin (Invitrogen 11058) and FBS (Sigma F9665) on a 96 wells microplate (Becton Dickinson 353072). After 16 hours medium waschanged to serum free medium. Galunisertib, as inhibitor ligand (Cayman CAY-15312) and recombinantHuman TGF-β2 (R&D Systems 302-B2-002) as activator of the ALK-5, were added in their correspondingwells and incubated following the instructions of the AlpahscreenAlphaLISA® SureFire® Ultra™ p-SMAD3(Ser423/425) Kit (Perkin Elmer ALSU-PSM3-A500).

Results

Table 2 shows the results of assays described below of some compounds of the present invention.

TABLE 2

| Example | Name | IC$_{50}$ range |
|---|---|---|
| 1 | N-benzyl-2-(3-(pyridin-2-yl)-4-(quinolin-4-yl)-1H-pyrazol-1-yl)acetamide | B |
| 9 | N-benzyl-2-(3-(6-methylpyridin-2-yl)-4-(quinolin-4-yl)-1H-pyrazol-1-yl)acetamide | A |
| 15 | N-(2-methylbenzyl)-2-(3-(6-methylpyridin-2-yl)-4-(quinolin-4-yl)-1H-pyrazol-1-yl)acetamide | B |
| 19 | 2-(3-(6-ethylpyridin-2-yl)-4-(quinolin-4-yl)-1H-pyrazol-1-yl)-N-(2-methylbenzyl)acetamide | B |
| 20 | N-(4-methylbenzyl)-2-(3-(6-methylpyridin-2-yl)-4-(quinolin-4-yl)-1H-pyrazol-1-yl)acetamide | A |
| 22 | N-(2-chlorobenzyl)-2-(3-(6-methylpyridin-2-yl)-4-(quinolin-4-yl)-1H-pyrazol-1-yl)acetamide | A |
| 24 | N-(2,6-difluorobenzyl)-2-(3-(6-methylpyridin-2-yl)-4-(quinolin-4-yl)-1H-pyrazol-1-yl)acetamide | A |
| 26 | N-(2,6-dimethylbenzyl)-2-(3-(6-methylpyridin-2-yl)-4-(quinolin-4-yl)-1H-pyrazol-1-yl)acetamide | B |
| 27 | N-(2-ethylbenzyl)-2-(3-(6-methylpyridin-2-yl)-4-(quinolin-4-yl)-1H-pyrazol-1-yl)acetamide | A |
| 28 | N-(2,6-dichlorobenzyl)-2-(3-(6-methylpyridin-2-yl)-4-(quinolin-4-yl)-1H-pyrazol-1-yl)acetamide | B |

Ranges:
A: IC$_{50}$ =<100 nM
B: 100 nM < IC$_{50}$ < 500 nM

As can be seen from the results described in tables above, the compounds of the present invention are potent inhibitors of transforming growth factor-β receptor I (TGFβRI/ALK5).

Plasma Pharmacokinetic Assay

The objective of this study was to investigate the plasma pharmacokinetics of some compounds of the present invention in male Sprague Dawley rats following a single oral administration. Three rats per compound were used in this study. Animals were administered with suspension formulation of each compound in 0.5% Tween-80 and 99.5% NaCMC (0.5% w/v in RO Water) by oral route at 5 mg/kg. The blood samples were collected from set of three rats at each time point in labelled micro centrifuge tube containing K$_2$EDTA solution as anticoagulant at 0.25, 0.5, 1, 2, 4, 6, 8, 12 and 24 hr (p.o.). Plasma samples were separated by centrifugation of whole blood and stored below −70±10° C. until bioanalysis. All samples were processed for analysis by protein precipitation using acetonitrile and analysed with fit-for-purpose LC-MS/MS method (LLOQ=1.01 ng/mL). Pharmacokinetic parameters were calculated using the non-compartmental analysis tool of Phoenix WinNonlin® (Version 7.0).

Main pharmacokinetic parameters obtained from some Examples are shown in Table 3 below.

TABLE 3

| Route | Analyte | Dose (mg/kg) | Tmax (hr) | Cmax (ng/mL) | AUClast (hr*ng/mL) | AUCinf (hr*ng/mL) |
|---|---|---|---|---|---|---|
| P.O. | Example 9 | 5 | 0.25 | 62.83 | 27.02 | 27.7 |
| | Example 15 | 5 | 0.25 | 75.76 | 35.09 | 39.42 |
| | Example 22 | 5 | 0.33 | 19.97 | 13.69 | 15.34 |
| | Example 24 | 5 | Concentrations were quantifiable only at 0.25 and 0.5 hr; not sufficient to calculate the PK parameters | | | |

Cmax: refers to the maximum plasma drug concentration obtained after oral administration of a drug between the time of dosing and the final observed time point.
AUClast: refers to the area under the curve from the time of dosing to the time of last observation that is greater than the limit of quantitation.
AUCinf: describe the total exposure to a drug.
Tmax: the time after administration of a Compound or drug when the maximum plasma concentration is reached.

From the PK data presented above, it can be concluded that the compounds of the present invention have a low systemic exposure after oral administration.

Metabolic Stability Assay

Human and rat recombinant microsomes from Tebu-Xenotech were employed in the assay. They content 0.5 mg/ml of protein. The following quantities were added to each well of a 96-well microplate.

| | Blank (µl) | Rat (µl) | Human (µl) |
|---|---|---|---|
| Phosphate buffer Na/K 50 mM pH 7.4 | 295 | 301.3 | 301.3 |
| MgCl$_2$ 30 mM | 50 | 50 | 50 |
| NADP 10 mM | 50 | 50 | 50 |
| Glucose 6-P 100 mM | 50 | 50 | 50 |
| Glucose 6-P DH 20 U/ml | 25 | 25 | 25 |
| Water | 25 | — | — |
| Rat microsomes | — | 18.7 | — |
| Human microsomes | — | — | 18.7 |
| Test compound | 5 | 5 | 5 |

Plates were incubated at 37° C. and 75 µL samples were taken at 0, 10, 20, 40 and 60 minutes. Samples were transferred to a microplate and 75 µl Acetonitrile were added for inactivating the microsomes, and 30 µl of H$_2$O for improving the chromatographic conditions and kept at 4° C. When all the samples were taken the plate was centrifuged at 46000 g for 30 min at 15° C. Supernatant was taken and injected in the UPLC-MS/MS.

Stationary phase: Reverse phase Acquity UPLC® BEH C18 1.7 μm (2.1 mm×50 mm) (Waters). Mobile phase: A: 0.1% formic; B:acetonitrile+0.1% formic acid. Flow: 0.6 ml/min. The chromatographic equipment employed was an UPLC QSM Waters Acquity. Compound concentrations were calculated from the UV peak areas. The response was linear in the range between 10 ng/ml and 0.3125 ng/ml. Metabolic stability was calculated from the logarithm of the remaining compound at each of the times evaluated.

Data Analysis

The data will be fitted to the one phase exponential decay equation using GraphPad Prism® software. The half-life ($t_{1/2}$) generated by the software will be reported. Intrinsic clearance will be calculated using the formula where, k=decay rate constant ($min^{-1}$).

$$Clint = \frac{k \times \text{volume of reaction mixture (uL)}}{\text{protein content (mg)}}$$

| | Rat | | Human | |
|---|---|---|---|---|
| Example | % remanent (sampling time 60 min) | Clint (μL/min * mg prot) | % remanent (sampling time 60 min) | Clint (μL/min * mg prot) |
| 20 | 0.02 | 381.1 | 0.01 | 215.6 |
| 22 | 0.14 | 644.4 | 0.03 | 378.4 |
| 24 | 0.01 | 359.9 | 0.05 | 307.3 |
| 26 | 0.08 | 825.6 | 0.05 | 622.4 |
| 27 | 0.31 | 600.5 | 0.53 | 505.0 |

The above analysed examples were unstable in the liver microsomes assay and showed high clearance in both evaluated species.

In an identification study of metabolite was identified Compound A. Said compound is 2-(3-(6-methylpyridin-2-yl)-4-(quinolin-4-yl)-1H-pyrazol-1-yl)acetic acid and has the following formula:

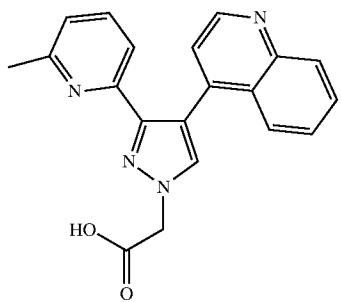 [SMILES: Cc1cccc(-c2nn(CC(=O)O)cc2-c2ccnc3ccccc23)n1]

$^1$H NMR (300 MHz, MeOD) δ 8.79 (d, J=4.6 Hz, 1H), 8.42 (br s, 1H), 8.09-7.85 (m, 3H), 7.77-7.63 (m, 1H), 7.59-7.28 (m, 4H), 7.08-6.96 (m, 1H), 4.97 (s, 2H), 2.08 (s, 3H).

HPLC-MS: Rt 13.025 miz 345.1 (MH$^+$).

Compound A was identified as the major metabolite of examples 9, 15, 20, 22, 24 and 26, among others.

The activity of Compound A against the TGFβR-1 was carried out according to the conditions described above, showing an IC$_{50}$ greater than 800 nM, Also was determined the intracellular TGF-beta kinase activity (ALK-5), showing an IC$_{50}$ greater than 5000 nM, The compounds of the invention have a low systemic exposure after oral, topical or ocular administration, due to their low metabolic stability, so they are especially suited for the treatment of diseases such as gastrointestinal diseases, such as inflammatory bowel diseases among there are Crohn's disease and ulcerative colitis, hepatic fibrosis and cancer, specifically gastric cancer, esophageal cancer and colorectal cancer; fibrotic skin diseases, such as scleroderma, nephrogenic fibrosing dermopathy, mixed connective tissue disease, scleromyxedema, scleredema, and eosinophilic fasciitis; fibrotic eye diseases such as dry eyes, age-related macular degeneration, scarring in the cornea and conjunctiva, post-cataract fibrosis, proliferative vitreoretinopathy and proliferative diabetic retinopathy.

Accordingly, the derivatives of the invention and pharmaceutically acceptable salts thereof, and pharmaceutical compositions comprising such compounds and/or salts thereof, may be used in a method of treatment of disorders of the human body which comprises administering to a subject requiring such treatment an effective amount of benzylamide derivatives of the present invention or a pharmaceutically acceptable salt thereof.

The present invention also provides pharmaceutical compositions which comprise, as an active ingredient, at least a benzylamide derivatives of formula (I) or a pharmaceutically acceptable salt thereof in association with, other therapeutics agents a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application.

Preferably, compounds of formula (I), pharmaceutically acceptable salts and compositions thereof are made up in a form suitable for oral, topical, ocular, rectal or percutaneous administration.

The pharmaceutically acceptable excipients, which are admixed with the active compound or salts of such compound, to form the compositions of this invention, are well known per se and the actual excipients used depend inter alia on the intended method of administering the compositions.

Compounds of formula (I), pharmaceutically salts thereof and compositions of this invention are preferably adapted for injectable and per os administration. In this case, the compositions for oral administration may take the form of tablets, retard tablets, sublingual tablets, capsules or liquid preparations, such as mixtures, elixirs, syrups or suspensions, all containing the compound of the invention; such preparations may be made by methods well-known in the art.

The diluents, which may be used in the preparation of the compositions, include those liquid and solid diluents, which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 2-2000 mg of active ingredient per day. Daily dosage may be administered in one or more treatments, preferably from 1 to 4 treatments, per day.

The present invention will be further illustrated by the following examples. The following are given by way of illustration and do not limit the scope of the invention in any way. The synthesis of the compounds of the invention is illustrated by the following examples including the preparation of the intermediates, which do not limit the scope of the invention in any way.

EXAMPLES

General. Reagents, solvents and starting products were acquired from commercial sources. The term "concentration" refers to the vacuum evaporation using a Büchi rotavapor. When indicated, the reaction products were purified by "flash" chromatography on silica gel (40-63 μm) with the indicated solvent system. The spectroscopic data were measured in a Varian Mercury 300 spectrometer. The HPLC-MS were performed on a Waters instrument equipped with an Alliance 2795 separation module, a UV-Vis W 2996 detector and a micromass ZQ 200.

Intermediate 1: ethyl 6-methylpicolinate

To a solution of 6-methylpicolinic acid (2.0 g, 14.58 mmol) in ethanol (50 mL) sulphuric acid (1.2 mL) was added and the mixture was heated to reflux for 22 hours and then concentrated to dryness. The residue was dissolved in water (50 mL), sodium bicarbonate was added until pH 8-9 and it was extracted with ethyl acetate (3×40 mL). The combined organic layers were dried over sodium sulfate and concentrated to afford a yellow oil (1.88 g, 78%).

$^1$H-NMR (300 MHz, CDCl$_3$): δ=7.95 (d, J=7.7 Hz, 1H), 7.72 (t, J=7.7 Hz, 1H), 7.34 (d, J=7.7 Hz, 1H), 4.49 (q, J=7.1 Hz, 2H), 2.67 (s, 3H), 1.44 (t, J=7.1 Hz, 3H).

HPLC-MS: Rt 8.258 m/z 166.5 [M+H]$^+$.

Intermediate 2: 1-(6-methylpyridin-2-yl)-2-(quinolin-4-yl)ethan-1-one

To a solution of lepidine (0.500 g, 3.49 mmol) in tetrahydrofuran (10 mL), cooled at −60° C., lithium bis(trimethylsilyl)amide (10.5 mL, 10.47 mmol. Solution 1M in tetrahydrofuran) was added and the reaction mixture was stirred at low temperature for 30 minutes. A solution of ethyl 6-methylpicolinate (0.634 g, 3.83 mmol) in tetrahydrofuran (5 mL) was added and the reaction mixture was stirred overnight, allowing the temperature to reach −10° C. The reaction mixture was quenched with ammonium chloride (aqueous saturated solution) and the solvent was removed in vacuo. The residue was dissolved in ethyl acetate (60 mL) and washed with ammonium chloride (2×50 mL, aqueous saturated solution). The organic layer was dried over sodium sulfate and concentrated. The reaction product was purified by flash chromatography on silica gel (40% EtOAc/Hexane) to afford a orange oil (0.423 g, 46%).

$^1$H-NMR (300 MHz, CDCl$_3$): δ=8.84 (d, J=4.4 Hz, 1H), 8.138-8.045 (m, 2H), 7.85 (d, J=7.6 Hz, 1H), 7.74-7.66 (m, 2H), 7.56-7.51 (m, 1H), 7.41 (d, J=4.4 Hz, 1H), 7.36 (dd, J=7.6, 0.5 Hz, 1H), 5.02 (s, 2H), 2.67 (s, 3H).

HPLC-MS: Rt 10.077 m/z 262.7 [M+H]$^+$.

Intermediate 3: 1-(6-ethylpyridin-2-yl)-2-(quinolin-4-yl)ethan-1-one

HPLC-MS: Rt 10.643 m/z 276.7[M+H]$^+$.

Intermediate 4: 4-(3-(6-methylpyridin-2-yl)-1H-pyrazol-4-yl)quinoline

To a solution of 1-(6-methylpyridin-2-yl)-2-(quinolin-4-yl)ethan-1-one (0.420 g, 1.60 mmol) in dimethylformamide (5 mL), acetic acid (0.330 mL, 5.76 mmol) and N,N-dimethylformamide-dimethyl acetal (0.640 mL, 4.80 mmol) were added and the reaction mixture was stirred at room temperature for 1 hour. Hydrazine monohydrate (1.75 mL, 35.84 mmol) was added and the solution was heated at 50° C. for 1 hour. The cooled reaction mixture was diluted with water (30 mL) and extracted with ethyl acetate (30 mL). The organic layer was washed with water (20 mL) and with brine (2×20 mL), dried over sodium sulfate and concentrated. The crude solid was recrystallized from acetonitrile to afford a yellow solid (0.335 g, 73%).

$^1$H-NMR (300 MHz, DMSO-d$_6$): δ=13.63 (br s, 1H), 8.81 (br s, 1H), 8.04 (d, J=9.6 Hz, 1H), 7.73-7.40 (m, 7H), 7.02 (m, 1H), 2.50 (s, 3H).

HPLC-MS: Rt 9.100 m/z 286.9 [M+H]$^+$.

Intermediate 5: 4-(3-(6-ethylpyridin-2-yl)-1H-pyrazol-4-yl)quinoline $^1$H-NMR (300 MHz, CDCl$_3$): δ=8.99 (d, J=4.4 Hz, 1H), 8.24 (d, J=8.4 Hz, 1H), 8.04 (s, 1H), 7.89-7.68 (m, 3H), 7.55-7.41 (m, 2H), 7.30-7.25 (m, 1H), 7.03 (d, J=7.8 Hz, 1H), 6.66 (d, J=7.8 Hz, 1H), 2.84 (q, J=7.6 Hz, 2H), 1.31 (t, J=7.6 Hz, 3H).

HPLC-MS: Rt 9.616 m/z 301.2 [M+H]$^+$.

Intermediate 6: (2-ethylphenyl)methanamine

To a solution of 2-ethylbenzonitrile (0.20 g, 1.52 mmol) in THF (8 mL) cooled down to 5° C. with the aid of an external ice/water bath external ice/H$_2$O bath, LiAlH4 (0.28 mg, 7.62 mmol) was added in portions. The reaction mixture was allowed to reach room temperature and stirred for 21 hour. H2O (3 mL) and NaOH (1 mL. Aqueous solution 36%) were added to the mixture and stirred for 5 min. The suspension was filtered through Celite washing with EtOAc (15 mL). The mother liquors were concentrated to dryness to give a pink oil (140 mg). The product was used in the next step without additional purification.

Intermediate 7: tert-butyl 4-((1,3-dioxoisoindolin-2-yl)methyl)benzoate

To a suspension of phtalimide (0.19 g, 1.32 mmol) and potassium carbonate (0.22 g, 1.59 mmol) in N,N-dimethylformamide (4 mL) added tert-butyl 4-(chloromethyl)benzoate (0.30 g, 1.32 mmol) was and the mixture was heated at 50° C. for 20 hours. The reaction mixture was cool down at room temperature, diluted with water (30 mL) and brine (20 mL) and extracted with ethyl acetate (2×15 mL). The combined organic extracts were dried over sodium sulfate and concentrated to afford a white solid (0.42 g, 95%).

$^1$H-NMR (300 MHz, CDC13): δ=7.93 (d, J=8.2 Hz, 2H), 7.85 (dd, J=5.3, 2.9 Hz, 2H), 7.72 (dd, J=5.3, 2.9 Hz, 2H), 7.44 (d, J=8.2 Hz, 2H), 4.88 (s, 2H), 1.56 (s, 9H).

Intermediate 8: tert-butyl 4-(aminomethyl)benzoate

To a suspension of tert-butyl 4-((1,3-dioxoisoindolin-2-yl)methyl)benzoate (0.41 g, 1.23 mmol) in ethanol (5 mL) hydrazine monohydrate (0.12 g, 2.46 mmol) was added and the mixture was refluxed under vigorous stirring for 2 hours. The reaction mixture was cooled to room temperature, hydrochloric acid solution 6M (22%) was added and the solution was heated for a further 5 minutes. Water (10 mL), ethyl acetate (10 mL) and an aqueous solution of hydrochloric acid 10%, to reach pH 1, were added. The layers were separated, and the organic layer was extracted with an aqueous solution of hydrochloric acid 10% (2×5 mL). The combined aqueous extracts were basified with an aqueous solution of sodium hydroxide 24% and extracted with ethyl acetate (2×10 mL). The combined organic extracts were dried over sodium sulfate and concentrated to afford a pale yellow oil (0.12 g, 48%).

$^1$H-NMR (300 MHz, CDCl$_3$): δ=7.84 (d, J=8.2 Hz, 2H), 7.24 (d, J=8.2 Hz, 2H), 3.81 (s, 2H), 1.48 (s, 9H).

Intermediate 9: N-benzyl-2-bromoacetamide

To a solution of benzylamine (1.5 g, 14.00 mmol) in THF (15 mL), cooled down to 5° C. with the aid of an external ice/water bath, bromoacetyl bromide (1.46 mL, 16.80 mmol) was added and the reaction mixture was stirred for 22 h, allowed to reach room temperature. The suspension resulting was filtered and the mother liquors were concentrated to dryness. The crude residue was purified by flash chromatography on silice gel (30%→50% EtOAc/Hexane) to afford a white solid (1.33 g, 42%).

HPLC-MS: Rt 8.327 m/z 226.0-228.1 [M−H]$^-$.

The following intermediates, from Intermediate 10 to Intermediate 26, were prepared following the procedure describe for Intermediate 9.

Intermediate 10:
2-bromo-N-(4-fluorobenzyl)acetamide

HPLC-MS: Rt 8.608 m/z 244.0-246.0 [M−H]$^-$.

Intermediate 11:
2-bromo-N-(4-chlorobenzyl)acetamide

HPLC-MS: Rt 9.273 m/z 262.2 [M−H]$^-$.

Intermediate 12:
2-bromo-N-(4-bromobenzyl)acetamide

This intermediate was used in the next step without additional purification.

Intermediate 13:
2-bromo-N-(4-methoxybenzyl)acetamide

HPLC-MS: Rt 6.125 m/z 258.1-259.9 [M+H]$^+$.

Intermediate 14:
2-bromo-N-(4-methylbenzyl)acetamide $^1$H-NMR (300 MHz, DMSO-d$_6$): δ=7.14 (s, 4H), 4.24 (d, J=5.9 Hz, 2H), 3.94 (s, 2H), 2.27 (s, 3H).
HPLC-MS: Rt 9.098 m/z 242.1-244.0 [M+H]$^+$.

Intermediate 15:
2-bromo-N-(4-(tert-butyl)benzyl)acetamide

HPLC-MS: Rt 10.406 m/z 282.0-284.2 [M−H]$^-$.

Intermediate 16:
2-bromo-N-(3-methylbenzyl)acetamide $^1$H-NMR (300 MHz, DMSO-d$_6$): δ=7.24-7.19 (m, 1H), 7.08-7.03 (m, 3H), 4.25 (d, J=5.9 Hz, 2H), 3.91 (s, 2H), 2.29 (s, 3H).

Intermediate 17:
2-bromo-N-(3-fluorobenzyl)acetamide $^1$H-NMR (300 MHz, DMSO-d$_6$): δ=8.83 (br s, 1H), 7.41-7.33 (m, 1H), 7.12-7.03 (m, 3H), 4.31 (d, J=6.0 Hz, 2H), 3.92 (s, 2H).
HPLC-MS: Rt 8.642 m/z 244.0-246.1 [M−H]$^-$.

Intermediate 18:
2-bromo-N-(3-chlorobenzyl)acetamide $^1$H-NMR (300 MHz, DMSO-d$_6$): δ=8.83 (br s, 1H), 7.51-7.08 (m, 4H), 4.30 (d, J=6.0 Hz, 2H), 3.92 (s, 2H).
HPLC-MS: Rt 9.266 m/z 260.0-262.1 [M−H]$^-$.

Intermediate 19:
2-bromo-N-(3-cyanobenzyl)acetamide $^1$H-NMR (300 MHz, DMSO-d$_6$): δ=7.78-7.66 (m, 2H), 7.66-7.45 (m, 2H), 4.35 (d, J=6.0 Hz, 2H), 3.94 (s, 2H).
HPLC-MS: Rt 8.018 m/z 251.0-253.1 [M−H]$^-$.

Intermediate 20:
2-bromo-N-(2-methylbenzyl)acetamide $^1$H-NMR (300 MHz, CDCl$_3$): δ=7.26-7.15 (m, 4H), 4.48 (d, J=5.5 Hz, 2H), 3.93 (s, 2H), 2.34 (s, 3H).
HPLC-MS: Rt 9.004 m/z 240.0 [M−H]$^-$.

Intermediate 21:
2-bromo-N-(2-fluorobenzyl)acetamide $^1$H-NMR (300 MHz, CDCl$_3$): δ=7.39-7.30 (m, 2H), 7.20-7.01 (m, 2H), 6.87 (s, 1H), 4.55 (d, J=6.0 Hz, 2H), 3.94 (s, 2H).
HPLC-MS: Rt 8.532 m/z 244.0-246.1 [M−H]$^-$.

Intermediate 22:
2-bromo-N-(2-chlorobenzyl)acetamide $^1$H-NMR (300 MHz, DMSO-d$_6$): δ=8.44 (br s, 1H), 7.25-6.79 (m, 4H), 3.98 (d, J=5.8 Hz, 2H), 3.56 (s, 1H).
HPLC-MS: Rt 9.097 m/z 264.0 [M−H]$^-$.

Intermediate 23: 2-bromo-N-(2,6-difluorobenzyl)acetamide $^1$H-NMR (300 MHz, DMSO-d$_6$): δ=8.70 (br s, 1H), 7.55-7.29 (m, 1H), 7.16-7.07 (m, 2H), 4.34 (d, J=5.3 Hz, 2H), 3.84 (s, 2H).

Intermediate 24: 2-bromo-N-(2-chlorobenzyl)acetamide $^1$H-NMR (300 MHz, DMSO-d$_6$): δ=8.34 (br s, 1H), 7.13-7.02 (m, 3H), 4.29 (d, J=4.8 Hz, 2H), 3.84 (s, 2H), 2.30 (s, 6H).
HPLC-MS: Rt 9.542 m/z 256.0 [M−H]$^-$.

Intermediate 25: 2-bromo-N-(2-ethylbenzyl)acetamide

HPLC-MS: Rt 9.526 m/z 253.9-256.0 [M−H]$^-$.

Intermediate 166: 2-bromo-N-(2,6-dichlorobenzyl)acetamide

HPLC-MS: Rt 9.466 m/z 294.0 [M−H]$^-$.

Intermediate 27: 2-bromo-N-(4-cyanobenzyl)acetamide

To a suspension of 4-(aminomethyl)benzonitrile hydrochloride (0.150 g, 0.890 mmol) in dichloromethane (4 mL), cooled down to 5° C. with the aid of an external ice/water bath, Et$_3$N (0.150 mL, 1.067 mmol) and bromoacetyl bromide (0.082 mL, 0.934 mmol) were added. The reaction mixture was stirred for 30 min, allowed to reach room temperature, diluted with dichloromethane (10 mL) and washed with H$_2$O (15 mL). The aqueous layer was extracted with dichloromethane (10 mL) and the organic extracts combined were dried over sodium sulfate and concentrated under reduced pressure. The residue was purified by flash chromatography on silica gel (50% EtOAc/hexanes) to give a beige solid (0.118 g, 52%).

$^1$H-NMR (300 MHz, DMSO-de): δ=8.89 (br s, 1H), 7.97-7.64 (m, 2H), 7.59-7.26 (m, 2H), 4.36 (d, J=6.0 Hz, 2H), 3.91 (s, 2H).

The following Intermediate 28 was prepared following the procedure describe for Intermediate 27.

Intermediate 28: tert-butyl 4-((2-bromoacetamido)methyl)benzoate $^1$H-NMR (300 MHz, DMSO-d$_6$): δ=8.87 (m, 1H), 7.85 (d, J=8.5 Hz, 2H), 7.36 (d, J=8.5 Hz, 2H), 4.35 (d, J=6.1 Hz, 2H), 3.92 (s, 2H), 1.53 (s, 9H).

Intermediate 29: tert-butyl 4-((2-(3-(pyridin-2-yl)-4-(quinolin-4-yl)-1H-pyrazol-1-yl)acetamido)methyl)benzoate This intermediate was prepared following the procedure describe for Example 1.
HPLC: Rt 18.982, 99.36%.

EXAMPLES

Example 1: N-benzyl-2-(3-(pyridin-2-yl)-4-(quinolin-4-yl)-1H-pyrazol-1-yl)acetamide To a solution of N-benzyl-2-bromoacetamide (0.100 g, 0.441 mmol) in acetonitrile (2 mL), K$_2$CO$_3$ (0.076 g, 0.550 mmol) and 4-(3-(pyridin-2-yl)-1H-pyrazol-4-yl)quinoline (0.100 g, 0.367 mmol) were added and the reaction mixture was refluxed for 6 h. N-benzyl-2-bromoacetamide (0.017 g, 0.073 mmol) was added and the mixture was refluxed other 1 h and allowed to reach room temperature. H$_2$O (10 mL) was added and extracted with EtOAc (3×5 mL). The organic extracts combined were dried over sodium sulfate and concentrated under reduced pressure. The residue was purified by C18 chromatography with a Combiflash system (5→100% H$_2$O/MeOH:MeCN 1:1) and by flash chromatography on silica gel (3% MeOH/CH$_2$Cl$_2$) to give a white solid (0.080 g, 52%).

$^1$H-NMR (500 MHz, CDC13): δ=8.89 (d, J=4.4 Hz, 1H), 8.42 (d, J=4.4, Hz, 1H), 8.16 (d, J=8.4 Hz, 1H), 7.74 (s, 1H), 7.72-7.66 (m, 2H), 7.45 (td, J=7.8, 1.8 Hz, 1H), 7.37-7.34 (m, 1H), 7.32-7.21 (m, 7H), 7.10 (ddd, J=7.8, 4.4, 1.8 Hz, 1H), 6.87 (br a, 1H), 5.05 (s, 2H), 4.52 (d, J=5.8 Hz, 2H).
HPLC-MS: Rt 16.753 m/z 420.2 [M+H]$^+$.

The following examples 2-4 were synthesized using the procedure described for the example 1 from the corresponding 4-(3-(pyridin-2-yl)-1H-pyrazol-4-yl)quinoline derivatives.

Example 2: N-(4-fluorobenzyl)-2-(3-(pyridin-2-yl)-4-(quinolin-4-yl)-1H-pyrazol-1-yl)acetamide $^1$H-NMR (300 MHz, DMSO-d$_6$): 8.98-8.65 (m, 2H), 8.19-7.95 (m, 3H), 7.87-7.58 (m, 4H), 7.51-7.25 (m, 4H), 7.26-7.05 (m, 3H), 5.06 (s, 2H), 4.36 (d, J=5.8 Hz, 2H).
HPLC-MS: Rt 16.989 m/z 438.2 [M+H]$^+$.

Example 3: N-(4-chlorobenzyl)-2-(3-(pyridin-2-yl)-4-(quinolin-4-yl)-1H-pyrazol-1-yl)acetamide $^1$H-NMR (300 MHz, DMSO-d$_6$): δ=8.99-8.62 (m, 2H), 8.22-7.89 (m, 3H), 7.88-7.50 (m, 4H), 7.53-7.22 (m, 6H), 7-17-7.13 (m, 1H), 5.06 (s, 2H), 4.36 (d, J=5.8 Hz, 2H).
HPLC-MS: Rt 17.839 m/z 454.2 [M+H]+.

Example 4: N-(4-bromobenzyl)-2-(3-(pyridin-2-yl)-4-(quinolin-4-yl)-1H-pyrazol-1-yl)acetamide $^1$H-NMR (300 MHz, DMSO-d$_6$): δ=8.84-8.80 (m, 2H), 8.18-7.93 (m, 3H), 7.88-7.60 (m, 4H), 7.60-7.20 (m, 6H), 7.18-7.14 (m, 1H), 5.06 (s, 2H), 4.34 (d, J=5.9 Hz, 2H).
HPLC-MS: Rt 18.057 m/z 498.0-500.0 [M+H]$^+$.

Example 5: N-(4-cyanobenzyl)-2-(3-(pyridin-2-yl)-4-(quinolin-4-yl)-1H-pyrazol-1-yl)acetamide To a suspension of 4-(3-(pyridin-2-yl)-1H-pyrazol-4-yhquinoline (0.060 g, 0.220 mmol) in tetrahydrofuran (3 mL), cooled down to 5° C. with the aid of an external ice/water bath, 60% sodium hydride (0.012 g, 0.308 mmol) was added and the mixture was stirred at the same temperature for 30 min. A solution of N-(4-cyanobenzyl)-2-bromoacetamide (0.078 g, 0.308 mmol) in a mixture of tetrahydrofuran (1 mL) and dimethylformamide (0.3 mL) was added dropwise and the mixture was stirred for 40 min. Other portion of N-(4-cyanobenzyl)-2-bromoacetamide (0.011 g, 0.048 mmol) was added stirring for 1.5 h additional. The reaction mixture was diluted with water (10 mL) and extracted with EtOAc (3×10 mL). The organic layers combined were dried over sodium sulfate and concentrated under reduced pressure. The residue was purified by flash chromatography on silica gel (2→4→5% MeOH/CH$_2$Cl$_2$)

and by C18 chromatography with a Combiflash system (5→100% H₂O/MeCN) to give a white solid (0.016 g, 16%).

¹H-NMR (500 MHz, DMSO-d₆): δ=8.89 (t, J=6.0 Hz, 1H), 8.83 (dd, J=4.4, 1.1 Hz, 1H), 8.16-8.07 (m, 2H), 8.03 (d, J=8.4 Hz, 1H), 7.85-7.61 (m, 5H), 7.53 (d, J=7.9 Hz, 2H), 7.44-7.36 (m, 1H), 7.32 (dd, J=4.4, 1.0 Hz, 1H), 7.20-7.12 (m, 1H), 5.10 (s, 2H), 4.47 (d, J=6.0 Hz, 2H).

HPLC-MS: Rt 16.091 m/z 445.1 [M+H]⁺.

The following examples 6-29 were synthesized using the procedure described for the example 5.

Example 6: N-(4-methoxybenzyl)-2-(3-(pyridin-2-yl)-4-(quinolin-4-yl)-1H-pyrazol-1-yl)acetamide ¹H-NMR (500 MHz, DMSO-d₆): δ=8.84 (d, J=4.5 Hz, 1H), 8.73 (t, J=5.9 Hz, 1H), 8.15-8.06 (m, 2H), 8.03 (d, J=8.6 Hz, 1H), 7.82-7.65 (m, 4H), 7.41-7.12 (m, 5H), 6.93-6.87 (m, 2H), 5.04 (s, 2H), 4.30 (d, J=5.8 Hz, 2H), 3.73 (s, 3H).

HPLC-MS: Rt 17.709 m/z 450.1[M+H]⁺.

Example 7: N-(4-methylbenzyl)-2-(3-(pyridin-2-yl)-4-(quinolin-4-yl)-1H-pyrazol-1-yl)acetamide ¹H-NMR (500 MHz, DMSO-d₆): δ=8.84 (d, J=4.4 Hz, 1H), 8.74 (t, J=5.9 Hz, 1H), 8.13-8.07 (m, 2H), 8.03 (d, J=9.1 Hz, 1H), 7.83-7.65 (m, 4H), 7.41 (ddd, J=8.2, 6.8, 1.3 Hz, 1H), 7.33 (d, J=4.4 Hz, 1H), 7.24-7.10 (m, 5H), 5.05 (s, 2H), 4.33 (d, J=5.8 Hz, 2H), 2.28 (s, 3H).

HPLC-MS: Rt 17.574 m/z 434.1 [M+H]⁺.

Example 8: N-(4-(tert-butyl)benzyl)-2-(3-(pyridin-2-yl)-4-(quinolin-4-yl)-1H-pyrazol-1-yl)acetamide ¹H-NMR (500 MHz, DMSO-d₆): δ=8.83 (d, J=4.4 Hz, 1H), 8.74 (t, J=5.8 Hz, 1H), 8.10-8.07 (m, 2H), 8.03 (d, J=8.4 Hz, 1H), 7.84-7.61 (m, 4H), 7.40 (t, J=7.6 Hz, 1H), 7.38-7.29 (m, 3H), 7.25 (d, J=8.2 Hz, 2H), 7.20-7.10 (m, 1H), 5.04 (s, 2H), 4.32 (d, J=5.8 Hz, 2H), 1.26 (s, 9H).

HPLC-MS: Rt 19.625 m/z 476.2 [M+H]⁺.

Example 9: N-benzyl-2-(3-(6-methylpyridin-2-yl)-4-(quinolin-4-yl)-1H-pyrazol-1-yl)acetamide ¹H-NMR (300 MHz, DMSO-d₆): δ=8.84 (d, J=4.5 Hz, 1H), 8.81-8.75 (m, 1H), 8.11 (d, J=1.2 Hz, 1H), 8.03 (d, J=8.1 Hz, 1H), 7.79-7.45 (m, 4H), 7.45-7.21 (m, 7H), 6.98 (d, J=7.5 Hz, 1H), 5.06 (s, 2H), 4.39 (d, J=5.7 Hz, 2H), 1.83 (s, 3H).

HPLC-MS: Rt 17.541 m/z 434.1 [M+H]⁺.

Example 10: N-(3-methylbenzyl)-2-(3-(pyridin-2-yl)-4-(quinolin-4-yl)-1H-pyrazol-1-yl)acetamide ¹H-NMR (300 MHz, DMSO-d₆): δ=8.90-8.62 (m, 2H), 8.19-7.89 (m, 3H), 7.88-7.53 (m, 4H), 7.51-6.90 (m, 7H), 5.06 (s, 2H), 4.34 (d, J=5.7 Hz, 2H), 2.27 (s, 3H).

HPLC-MS: Rt 17.625 m/z 433.9 [M+H]⁺.

Example 11: N-(3-fluorobenzyl)-2-(3-(pyridin-2-yl)-4-(quinolin-4-yl)-1H-pyrazol-1-yl)acetamide ¹H-NMR (300 MHz, DMSO-d₆): δ=8.83 (d, J=4.3 Hz, 2H), 8.13 (s, 1H), 8.10 (d, J=5.2 Hz, 1H), 8.03 (d, J=8.4 Hz, 1H), 7.84-7.65 (m, 4H), 7.48-7.27 (m, 3H), 7.22-7.02 (m, 4H), 5.08 (s, 2H), 4.40 (d, J=5.9 Hz, 2H).

HPLC-MS: Rt 16.970 m/z 438.0 [M+H]⁺.

Example 12: N-(3-chlorobenzyl)-2-(3-(pyridin-2-yl)-4-(quinolin-4-yl)-1H-pyrazol-1-yl)acetamide ¹H-NMR (300 MHz, DMSO-d₆): δ=8.86-8.82 (m, 2H), 8.12 (s, 1H), 8.09 (d, J=5.1 Hz, 1H), 8.03 (d, J=8.4 Hz, 1H), 7.88-7.61 (m, 4H), 7.48-7.23 (m, 6H), 7.18-7.12 (m, 1H), 5.08 (s, 2H), 4.39 (d, J=5.8 Hz, 2H).

HPLC-MS: Rt 17.747 m/z 454.1 [M+H]⁺.

Example 13: N-(3-cyanobenzyl)-2-(3-(pyridin-2-yl)-4-(quinolin-4-yl)-1H-pyrazol-1-yl)acetamide ¹H-NMR (300 MHz, DMSO-d₆): δ=9.03-8.70 (m, 2H), 8.14 (d, J=1.7 Hz, 1H), 8.09 (d, J=4.9 Hz, 1H), 8.04 (d, J=8.3 Hz, 1H), 7.86-7.63 (m, 7H), 7.56 (t, J=7.6 Hz, 1H), 7.42 (t, J=7.6 Hz, 1H), 7.35 (dd, J=4.9, 1.7 Hz, 1H), 7.16 (dd, J=6.9, 5.0 Hz, 1H), 5.10 (s, 2H), 4.44 (d, J=5.9 Hz, 2H).

HPLC-MS: Rt 16.152 m/z 445.1 [M+H]⁺.

Example 14: N-(2-methylbenzyl)-2-(3-(pyridin-2-yl)-4-(quinolin-4-yl)-1H-pyrazol-1-yl)acetamide ¹H-NMR (300 MHz, DMSO-d₆): δ=8.85-8.82 (m, 1H), 8.68 (br s, 1H), 8.18-7.95 (m, 3H), 7.88-7.60 (m, 4H), 7.49-7.08 (m, 7H), 5.06 (s, 2H), 4.35 (d, J=5.4 Hz, 2H), 2.30 (s, 3H).

HPLC-MS: Rt 17.417 m/z 434.1 [M+H]⁺.

Example 15: N-(2-methylbenzyl)-2-(3-(6-methylpyridin-2-yl)-4-(quinolin-4-yl)-1H-pyrazol-1-yl)acetamide ¹H-NMR (300 MHz, DMSO-d₆): δ=8.84 (d, J=4.5 Hz, 1H), 8.68 (br s, 1H), 8.12 (s, 1H), 8.03 (d, J=8.4 Hz, 1H), 7.78-7.23 (m, 7H), 7.19 (br s, 3H), 6.98 (d, J=7.5 Hz, 1H), 5.06 (s, 2H), 4.35 (d, J=5.6 Hz, 2H), 2.31 (s, 3H), 1.82 (s, 3H).

HPLC-MS: Rt 18.202 m/z 448.1 [M+H]⁺.

Example 16: N-(2-fluorobenzyl)-2-(3-(pyridin-2-yl)-4-(quinolin-4-yl)-1H-pyrazol-1-yl)acetamide ¹H-NMR (300 MHz, DMSO-d₆): δ=8.93-8.70 (m, 2H), 8.24-7.91 (m, 3H), 7.91-7.60 (m, 4H), 7.55-7.02 (m, 7H), 5.07 (s, 2H), 4.41 (d, J=5.5 Hz, 2H).

HPLC-MS: Rt 16.941 m/z 438.1 [M+H]⁺.

Example 17: N-(2-fluorobenzyl)-2-(3-(6-methylpyridin-2-yl)-4-(quinolin-4-yl)-1H-pyrazol-1-yl)acetamide ¹H-NMR (300 MHz, DMSO-d₆): δ=8.85-8.80 (m, 2H), 8.11 (s, 1H), 8.03 (d, J=8.4 Hz, 1H), 7.78-7.11 (m, 10H), 6.98 (d, J=7.5 Hz, 1H), 5.07 (s, 2H), 4.42 (d, J=5.6 Hz, 2H), 1.83 (s, 3H).

HPLC-MS: Rt 17.628 m/z 452.0 [M+H]⁺.

Example 18: N-benzyl-2-(3-(6-ethylpyridin-2-yl)-4-(quinolin-4-yl)-1H-pyrazol-1-yl)acetamide ¹H-NMR (300 MHz, DMSO-d₆): δ=8.85 (d, J=4.4 Hz, 1H), 8.78 (t, J=5.9 Hz, 1H), 8.09 (s, 1H), 8.02 (d, J=9.3 Hz, 1H), 7.72-7.62 (m, 4H), 7.42-7.16 (m, 7H), 6.95 (dd, J=6.7, 2.0 Hz, 1H), 5.07 (s, 2H), 4.39 (d, J=5.8 Hz, 2H), 2.10 (q, J=7.5 Hz, 2H), 0.28 (t, J=7.5 Hz, 3H).

HPLC-MS: Rt 18.386 m/z 448.1 [M+H]⁺.

Example 19: 2-(3-(6-ethylpyridin-2-yl)-4-(quinolin-4-yl)-1H-pyrazol-1-yl)-N-(2-methylbenzyl)acetamide $^1$H-NMR (300 MHz, DMSO-d$_6$): δ=9.04 (d, J=4.4 Hz, 1H), 8.86 (t, J=5.7 Hz, 1H), 8.28 (s, 1H), 8.21 (d, J=8.4 Hz, 1H), 7.92-7.77 (m, 4H), 7.62-7.45 (m, 3H), 7.38 (m, 3H), 7.14 (dd, J=6.4, 2.4 Hz, 1H), 5.25 (s, 2H), 4.55 (d, J=5.6 Hz, 2H), 2.50 (s, 3H), 2.29 (q, J=7.5 Hz, 2H), 0.46 (t, J=7.5 Hz, 3H).

HPLC-MS: Rt 19.102 m/z 462.1 [M+H]$^+$.

Example 20: N-(4-methylbenzyl)-2-(3-(6-methylpyridin-2-yl)-4-(quinolin-4-yl)-1H-pyrazol-1-yl)acetamide $^1$H-NMR (300 MHz, DMSO-d$_6$): δ=8.84 (d, J=4.4 Hz, 1H), 8.75 (t, J=5.9 Hz, 1H), 8.11 (s, 1H), 8.03 (d, J=8.3 Hz, 1H), 7.75-7.47 (m, 4H), 7.44-7.31 (m, 2H), 7.26-7.10 (m, 4H), 6.98 (d, J=7.5 Hz, 1H), 5.05 (s, 2H), 4.33 (d, J=5.8 Hz, 2H), 2.28 (s, 3H), 1.83 (s, 3H).

HPLC-MS: Rt 16.848 m/z 448.1 [M+H]$^+$.

Example 21: N-(2-chlorobenzyl)-2-(3-(pyridin-2-yl)-4-(quinolin-4-yl)-1H-pyrazol-1-yl)acetamide $^1$H-NMR (300 MHz, DMSO-d$_6$): δ=8.85-8.79 (m, 1H), 8.18-8.06 (m, 2H), 8.03 (d, J=8.5 Hz, 1H), 7.88-7.62 (m, 4H), 7.57-7.23 (m, 6H), 7.24-7.06 (m, 1H), 5.10 (s, 2H), 4.44 (d, J=5.7 Hz, 2H).

HPLC-MS: Rt 17.627 m/z 454.0 [M+H]$^+$.

Example 22: N-(2-chlorobenzyl)-2-(3-(6-methylpyridin-2-yl)-4-(quinolin-4-yl)-1H-pyrazol-1-yl)acetamide $^1$H-NMR (300 MHz, DMSO-d$_6$): δ=8.89-8.73 (m, 2H), 8.13 (s, 1H), 8.03 (d, J=8.3 Hz, 1H), 7.77-7.26 (m, 10H), 6.98 (d, J=7.4 Hz, 1H), 5.11 (s, 2H), 4.45 (d, J=5.7 Hz, 2H), 1.83 (s, 3H).

HPLC-MS: Rt 18.273 m/z 468.0 [M+H]$^+$.

Example 23: N-(2,6-difluorobenzyl)-2-(3-(pyridin-2-yl)-4-(quinolin-4-yl)-1H-pyrazol-1-yl)acetamide $^1$H-NMR (300 MHz, DMSO-d$_6$): δ=8.83 (d, J=4.5 Hz, 1H), 8.77 (t, J=5.4 Hz, 1H), 8.15-7.96 (m, 3H), 7.82-7.63 (m, 4H), 7.50-7.34 (m, 2H), 7.31 (d, J=4.5 Hz, 1H), 7.22-7.04 (m, 3H), 4.99 (s, 2H), 4.42 (d, J=5.1 Hz, 2H).

HPLC-MS: Rt 16.731 m/z 455.9 [M+H]$^+$.

Example 24: N-(2,6-difluorobenzyl)-2-(3-(6-methylpyridin-2-yl)-4-(quinolin-4-yl)-1H-pyrazol-1-yl)acetamide $^1$H-NMR (300 MHz, DMSO-d$_6$): δ=8.84 (d, J=4.4 Hz, 1H), 8.76 (t, J=5.3 Hz, 1H), 8.11-7.97 (m, 2H), 7.75-7.28 (m, 7H), 7.13 (t, J=7.8 Hz, 2H), 6.97 (d, J=7.5 Hz, 1H), 4.99 (s, 2H), 4.43 (d, J=5.3 Hz, 2H), 1.83 (s, 3H).

HPLC-MS: Rt 17.513 m/z 470.0 [M+H]$^+$.

Example 25: N-(2,6-dimethylbenzyl)-2-(3-(pyridin-2-yl)-4-(quinolin-4-yl)-1H-pyrazol-1-yl)acetamide $^1$H-NMR (300 MHz, DMSO-d$_6$): δ=8.83 (d, J=4.4 Hz, 1H), 8.43-8.39 (m, 2H), 8.16-8.06 (m, 2H), 8.03 (d, J=8.4 Hz, 1H), 7.81-7.63 (m, 4H), 7.48-7.35 (m, 1H), 7.32 (d, J=4.5 Hz, 1H), 7.21-6.97 (m, 4H), 4.99 (s, 2H), 4.37 (d, J=4.8 Hz, 2H), 2.35 (s, 6H).

HPLC-MS: Rt 18.188 m/z 448.1 [M+H]$^+$.

Example 26: N-(2,6-dimethylbenzyl)-2-(3-(6-methylpyridin-2-yl)-4-(quinolin-4-yl)-1H-pyrazol-1-yl)acetamide $^1$H-NMR (300 MHz, DMSO-d$_6$): δ=8.83 (d, J=4.4 Hz, 1H), 8.40 (t, J=4.9 Hz, 1H), 8.08 (s, 1H), 8.02 (dd, J=8.9, 1.3 Hz, 1H), 7.77-7.27 (m, 6H), 7.18-6.92 (m, 4H), 4.98 (s, 2H), 4.37 (d, J=4.8 Hz, 2H), 2.35 (s, 6H), 1.82 (s, 3H).

HPLC-MS: Rt 18.911 m/z 462.1 [M+H]$^+$.

Example 27: N-(2-ethylbenzyl)-2-(3-(6-methylpyridin-2-yl)-4-(quinolin-4-yl)-1H-pyrazol-1-yl)acetamide $^1$H-NMR (300 MHz, DMSO-d$_6$): δ=8.84 (d, J=4.5 Hz, 1H), 8.69 (t, J=5.6 Hz, 1H), 8.11 (s, 1H), 8.03 (d, J=8.3 Hz, 1H), 7.77-7.13 (m, 10H), 6.98 (d, J=7.5 Hz, 1H), 5.05 (s, 2H), 4.39 (d, J=5.6 Hz, 2H), 2.66 (q, J=7.5 Hz, 2H), 1.17 (t, J=7.5 Hz, 3H).

HPLC-MS: Rt 18.940 m/z 462.1 [M+H]$^+$.

Example 28: N-(2,6-dichlorobenzyl)-2-(3-(6-methylpyridin-2-yl)-4-(quinolin-4-yl)-1H-pyrazol-1-yl)acetamide $^1$H-NMR (300 MHz, DMSO-d$_6$): δ=8.84 (d, J=4.5 Hz, 1H), 8.61 (m, 1H), 8.09 (s, 1H), 8.03 (d, J=8.6 Hz, 1H), 7.75-7.28 (m, 9H), 6.98 (d, J=7.5 Hz, 1H), 5.01 (s, 2H), 4.61 (d, J=4.6 Hz, 2H), 1.83 (s, 3H).

HPLC-MS: Rt 18.877 m/z 502.1 [M+H]$^+$.

Example 29: 4-((2-(3-(pyridin-2-yl)-4-(quinolin-4-yl)-1H-pyrazol-1-yl)acetamido)methyl)benzoic acid hydrochloride A suspension of tert-butyl 44(2-(3-(pyridin-2-yl)-4-(quinolin-4-yl)-1H-pyrazol-1-yl)acetamido)methyl)benzoate (0.106 g, 0.204 mmol) in hydrochloroic acid (9 mL. Disolution 4M in dioxane) was heated at 80° C. for 1 hour. The reaction was cooled and concentrated in vacuo. The residue was purified by C18 chromatography with a Combiflash system (5→100% H$_2$O:MeCN) to afford a white solid (0.033 g, 33%).

$^1$H-NMR (300 MHz, DMSO-d$_6$): δ=9.04 (d, J=5.3 Hz, 1H), 8.95 (m, 1H), 8.27 (s, 1H), 8.21 (d, J=8.2 Hz, 1H), 8.09 (d, J=4.1 Hz, 1H), 7.92-7.79 (m, 5H), 7.63-7.57 (m, 2H), 7.45 (d, J=7.6 Hz, 2H), 7.21 (m, 1H), 5.13 (s, 2H), 4.45 (d, J=5.3 Hz, 2H).

HPLC-MS: Rt 13.067 m/z 464.2 [M+H]$^+$.

The invention claimed is:
1. A compound of formula (I):

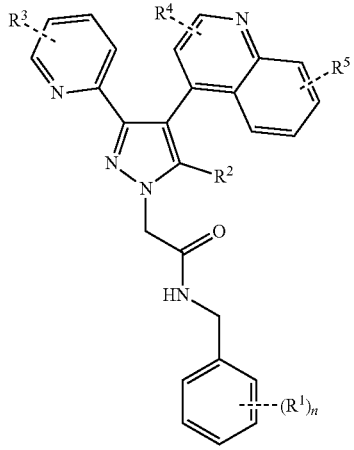

wherein:
R¹ is 1 or 2 groups independently selected from:
  a) halogen atom,
  b) linear or branched $C_1$-$C_6$ alkyl optionally substituted by 1, 2 or 3 halogen atoms,
  c) cyano group,
  d) $C_1$-$C_3$ alkoxy, and
  e) —COOH,
R² is a group selected from:
  a) hydrogen atom, and
  b) $C_1$-$C_3$ alkyl,
R³ is a group selected from:
  a) hydrogen atom,
  b) $C_1$-$C_3$ alkyl optionally substituted by 1, 2 or 3 halogen atoms, and
  c) halogen atom,
R⁴ and R⁵ independently are selected from:
  a) hydrogen atom,
  b) $C_1$-$C_3$ alkyl optionally substituted by 1, 2 or 3 halogen atoms, and
  c) halogen atoms,
n has a value of 0, 1 or 2,
or a pharmaceutically acceptable salt thereof.

2. The compound or salt of claim 1 wherein each of R², R⁴, and R⁵ are hydrogen atoms.

3. The compound or salt of claim 1, wherein
n is 0 or
n is 1 or 2 and each R¹ independently is a halogen atom.

4. The compound or salt of claim 3, wherein n is 1 or 2 and each R¹ independently is a halogen atom.

5. The compound or salt of claim 4, wherein each R¹ is selected from the group consisting of a fluorine atom and a chlorine atom.

6. The compound or salt of claim 1, wherein R³ is a group selected from a hydrogen atom, an ethyl group, and a methyl group.

7. The compound or salt of claim 6, wherein R³ is a methyl group.

8. The compound or salt of claim 1, wherein R², R⁴, and R⁵ independently are hydrogen atoms,
n is 0 or n is 1 or 2 and each R¹ independently is a halogen atom, and R³ is a group selected from a hydrogen atom, an ethyl group, and a methyl group.

9. The compound or salt of claim 8, wherein
n is 1 or 2,
each R¹ is independently selected from the group consisting of a fluorine atom and a chlorine atom, and
R³ is a methyl group.

10. The compound or salt according to claim 1, wherein the compound is selected from the group consisting of:
N-benzyl-2-(3-(pyridin-2-yl)-4-(quinolin-4-yl)-1H-pyrazol-1-yl) acetamide;
N-(4-fluorobenzyl)-2-(3-(pyridin-2-yl)-4-(quinolin-4-yl)-1H-pyrazol-1-yl) acetamide;
N-(4-chlorobenzyl)-2-(3-(pyridin-2-yl)-4-(quinolin-4-yl)-1H-pyrazol-1-yl) acetamide;
N-(4-bromobenzyl)-2-(3-(pyridin-2-yl)-4-(quinolin-4-yl)-1H-pyrazol-1-yl) acetamide;
N-(4-cyanobenzyl)-2-(3-(pyridin-2-yl)-4-(quinolin-4-yl)-1H-pyrazol-1-yl) acetamide;
N-(4-methoxybenzyl)-2-(3-(pyridin-2-yl)-4-(quinolin-4-yl)-1H-pyrazol-1-yl) acetamide;
N-(4-methylbenzyl)-2-(3-(pyridin-2-yl)-4-(quinolin-4-yl)-1H-pyrazol-1-yl) acetamide;
N-(4-(tert-butyl)benzyl)-2-(3-(pyridin-2-yl)-4-(quinolin-4-yl)-1H-pyrazol-1-yl) acetamide;
N-benzyl-2-(3-(6-methylpyridin-2-yl)-4-(quinolin-4-yl)-1H-pyrazol-1-yl) acetamide;
N-(3-methylbenzyl)-2-(3-(pyridin-2-yl)-4-(quinolin-4-yl)-1H-pyrazol-1-yl) acetamide;
N-(3-fluorobenzyl)-2-(3-(pyridin-2-yl)-4-(quinolin-4-yl)-1H-pyrazol-1-yl) acetamide;
N-(3-chlorobenzyl)-2-(3-(pyridin-2-yl)-4-(quinolin-4-yl)-1H-pyrazol-1-yl) acetamide;
N-(3-cyanobenzyl)-2-(3-(pyridin-2-yl)-4-(quinolin-4-yl)-1H-pyrazol-1-yl) acetamide;
N-(2-methylbenzyl)-2-(3-(pyridin-2-yl)-4-(quinolin-4-yl)-1H-pyrazol-1-yl) acetamide;
N-(2-methylbenzyl)-2-(3-(6-methylpyridin-2-yl)-4-(quinolin-4-yl)-1H-pyrazol-1-yl) acetamide;
N-(2-fluorobenzyl)-2-(3-(pyridin-2-yl)-4-(quinolin-4-yl)-1H-pyrazol-1-yl) acetamide;
N-(2-fluorobenzyl)-2-(3-(6-methylpyridin-2-yl)-4-(quinolin-4-yl)-1H-pyrazol-1-yl) acetamide;
N-benzyl-2-(3-(6-ethylpyridin-2-yl)-4-(quinolin-4-yl)-1H-pyrazol-1-yl) acetamide;
2-(3-(6-ethylpyridin-2-yl)-4-(quinolin-4-yl)-1H-pyrazol-1-yl)-N-(2-methylbenzyl) acetamide;
N-(4-methylbenzyl)-2-(3-(6-methylpyridin-2-yl)-4-(quinolin-4-yl)-1H-pyrazol-1-yl) acetamide;
N-(2-chlorobenzyl)-2-(3-(pyridin-2-yl)-4-(quinolin-4-yl)-1H-pyrazol-1-yl) acetamide;
N-(2-chlorobenzyl)-2-(3-(6-methylpyridin-2-yl)-4-(quinolin-4-yl)-1H-pyrazol-1-yl) acetamide;
N-(2,6-difluorobenzyl)-2-(3-(pyridin-2-yl)-4-(quinolin-4-yl)-1H-pyrazol-1-yl) acetamide;
N-(2,6-difluorobenzyl)-2-(3-(6-methylpyridin-2-yl)-4-(quinolin-4-yl)-1H-pyrazol-1-yl) acetamide;
N-(2,6-dimethylbenzyl)-2-(3-(pyridin-2-yl)-4-(quinolin-4-yl)-1H-pyrazol-1-yl) acetamide;
N-(2,6-dimethylbenzyl)-2-(3-(6-methylpyridin-2-yl)-4-(quinolin-4-yl)-1H-pyrazol-1-yl) acetamide;
N-(2-ethylbenzyl)-2-(3-(6-methylpyridin-2-yl)-4-(quinolin-4-yl)-1H-pyrazol-1-yl) acetamide;
N-(2,6-dichlorobenzyl)-2-(3-(6-methylpyridin-2-yl)-4-(quinolin-4-yl)-1H-pyrazol-1-yl) acetamide;
4-((2-(3-(pyridin-2-yl)-4-(quinolin-4-yl)-1H-pyrazol-1-yl) acetamido)methyl)benzoic acid; and
a pharmaceutically acceptable salt of any one thereof.

11. A pharmaceutical composition comprising the compound or salt of claim 1 and a pharmaceutically acceptable diluent or carrier.

12. A method of inhibiting transforming growth factor-β receptor I (TGFβRI/ALK5) in a subject, the method comprising: administering to the subject the compound or salt of claim 1.

13. The method according to claim 12 wherein the subject suffers from a disease or pathological condition selected from the group consisting of gastrointestinal diseases, hepatic fibrosis, cancer, fibrotic skin diseases, and fibrotic eye diseases.

14. The composition of claim 11, the composition further comprising a therapeutic agent used for the treatment and/or prevention of a disease selected from the group consisting of gastrointestinal diseases, hepatic fibrosis, cancer, fibrotic skin diseases, and fibrotic eye diseases.

15. A method for the treatment of a disease or pathological condition susceptible to amelioration by inhibition of transforming growth factor-β receptor I (TGFβRI/ALK5) in a subject in need thereof, the method comprising: administering to the subject the compound or salt of claim 1.

16. The method according to claim 15, wherein the disease or pathological condition is selected from the group consisting of gastrointestinal diseases, hepatic fibrosis, cancer, fibrotic skin diseases, and fibrotic eye diseases.

17. The method according to claim 15 wherein the disease or pathological condition is selected from the group consisting of Crohn's disease, ulcerative colitis, gastric cancer, esophageal cancer, colorectal cancer, scleroderma, nephrogenic fibrosing dermopathy, mixed connective tissue disease, scleromyxedema, eosinophilic fasciitis, dry eyes, age-related macular degeneration, scarring in the cornea, scarring in the conjunctiva, post-cataract fibrosis, proliferative vitreoretinopathy and proliferative diabetic retinopathy.

18. The composition of claim 11, the composition further comprising a therapeutic agent used for the treatment and/or prevention of a disease selected from the group consisting of Crohn's disease, ulcerative colitis, gastric cancer, esophageal cancer, colorectal cancer, scleroderma, nephrogenic fibrosing dermopathy, mixed connective tissue disease, scleromyxedema, eosinophilic fasciitis, dry eyes, age-related macular degeneration, scarring in the cornea, scarring in the conjunctiva, post-cataract fibrosis, proliferative vitreoretinopathy and proliferative diabetic retinopathy.

19. The compound of claim 1 not in the form of a pharmaceutically acceptable salt.

20. The compound of claim 1 in the form of a pharmaceutically acceptable salt.

21. The compound of claim 1 which is N-(2,6-difluorobenzyl)-2-(3-(6-methylpyridin-2-yl)-4-(quinolin-4-yl)-1H-pyrazol-1-yl) acetamide.

22. The compound or salt of claim 1 which is a pharmaceutically acceptable salt of N-(2,6-difluorobenzyl)-2-(3-(6-methylpyridin-2-yl)-4-(quinolin-4-yl)-1H-pyrazol-1-yl) acetamide.

23. The method according to claim 13, wherein the disease or pathological condition is a gastrointestinal disease.

24. The method according to claim 23, wherein the gastrointestinal disease is Crohn's disease.

25. The method according to claim 23, wherein the compound is N-(2,6-difluorobenzyl)-2-(3-(6-methylpyridin-2-yl)-4-(quinolin-4-yl)-1H-pyrazol-1-yl) acetamide.

26. The method according to claim 23, wherein the pharmaceutically acceptable salt is a pharmaceutically acceptable salt of N-(2,6-difluorobenzyl)-2-(3-(6-methylpyridin-2-yl)-4-(quinolin-4-yl)-1H-pyrazol-1-yl) acetamide.

27. The method according to claim 24, wherein the compound is N-(2,6-difluorobenzyl)-2-(3-(6-methylpyridin-2-yl)-4-(quinolin-4-yl)-1H-pyrazol-1-yl) acetamide.

28. The method according to claim 24, wherein the pharmaceutically acceptable salt is a pharmaceutically acceptable salt of N-(2,6-difluorobenzyl)-2-(3-(6-methylpyridin-2-yl)-4-(quinolin-4-yl)-1H-pyrazol-1-yl) acetamide.

29. The method according to claim 16, wherein the disease or pathological condition is a gastrointestinal disease.

30. The method according to claim 29, wherein the gastrointestinal disease is Crohn's disease.

31. The method according to claim 29, wherein the compound is N-(2,6-difluorobenzyl)-2-(3-(6-methylpyridin-2-yl)-4-(quinolin-4-yl)-1H-pyrazol-1-yl) acetamide.

32. The method according to claim 29, wherein the pharmaceutically acceptable salt is a pharmaceutically acceptable salt of N-(2,6-difluorobenzyl)-2-(3-(6-methylpyridin-2-yl)-4-(quinolin-4-yl)-1H-pyrazol-1-yl) acetamide.

33. The method according to claim 30, wherein the compound is N-(2,6-difluorobenzyl)-2-(3-(6-methylpyridin-2-yl)-4-(quinolin-4-yl)-1H-pyrazol-1-yl) acetamide.

34. The method according to claim 30, wherein the pharmaceutically acceptable salt is a pharmaceutically acceptable salt of N-(2,6-difluorobenzyl)-2-(3-(6-methylpyridin-2-yl)-4-(quinolin-4-yl)-1H-pyrazol-1-yl) acetamide.

* * * * *